US011957497B2

(12) United States Patent
Chui et al.

(10) Patent No.: US 11,957,497 B2
(45) Date of Patent: *Apr. 16, 2024

(54) SYSTEM AND METHOD FOR HIERARCHICAL MULTI-LEVEL FEATURE IMAGE SYNTHESIS AND REPRESENTATION

(71) Applicant: Hologic, Inc., Marlborough, MA (US)

(72) Inventors: Haili Chui, Santa Clara, CA (US); Liyang Wei, San Jose, CA (US); Jun Ge, Cupertino, CA (US); Xiangwei Zhang, Fremont, CA (US); Nikolaos Gkanatsios, Danbury, CT (US)

(73) Assignee: HOLOGIC, INC, Marlborough, MA (US)

( * ) Notice: Subject to any disclaimer, the term of this patent is extended or adjusted under 35 U.S.C. 154(b) by 204 days.

This patent is subject to a terminal disclaimer.

(21) Appl. No.: 17/692,989

(22) Filed: Mar. 11, 2022

(65) Prior Publication Data

US 2022/0192615 A1 Jun. 23, 2022

Related U.S. Application Data

(63) Continuation of application No. 16/497,764, filed as application No. PCT/US2018/024911 on Mar. 28, 2018, now Pat. No. 11,399,790.
(Continued)

(51) Int. Cl.
*G06K 9/00* (2022.01)
*A61B 6/00* (2006.01)
(Continued)

(52) U.S. Cl.
CPC .............. *A61B 6/502* (2013.01); *A61B 6/025* (2013.01); *G06F 18/254* (2023.01);
(Continued)

(58) Field of Classification Search
CPC .............. G06K 9/00; A61B 6/00; A61B 6/466
(Continued)

(56) References Cited

U.S. PATENT DOCUMENTS

| 3,502,878 A | 3/1970 | Stewart |
| 3,863,073 A | 1/1975 | Wagner |

(Continued)

FOREIGN PATENT DOCUMENTS

| AU | 2014339982 | 4/2015 |
| CN | 1846622 | 10/2006 |

(Continued)

OTHER PUBLICATIONS

Kopans, Daniel B., "Breast Imaging", 3rd Edition, Lippincott Williams and Wilkins, published Nov. 2, 2006, pp. 960-967.
(Continued)

*Primary Examiner* — Seyed H Azarian
(74) *Attorney, Agent, or Firm* — MERCHANT & GOULD P.C.

(57) ABSTRACT

A method for processing breast tissue image data includes processing the image data to generate a set of image slices collectively depicting the patient's breast; for each image slice, applying one or more filters associated with a plurality of multi-level feature modules, each configured to represent and recognize an assigned characteristic or feature of a high-dimensional object; generating at each multi-level feature module a feature map depicting regions of the image slice having the assigned feature; combining the feature maps generated from the plurality of multi-level feature modules into a combined image object map indicating a probability that the high-dimensional object is present at a particular location of the image slice; and creating a 2D synthesized image identifying one or more high-dimen-
(Continued)

sional objects based at least in part on object maps generated for a plurality of image slices.

16 Claims, 9 Drawing Sheets

Related U.S. Application Data

(60) Provisional application No. 62/478,977, filed on Mar. 30, 2017.

(51) Int. Cl.
| | |
|---|---|
| *A61B 6/02* | (2006.01) |
| *A61B 6/50* | (2024.01) |
| *G06F 18/25* | (2023.01) |
| *G06T 7/00* | (2017.01) |
| *G06T 17/10* | (2006.01) |
| *G06V 10/80* | (2022.01) |
| *G06V 30/24* | (2022.01) |

(52) U.S. Cl.
CPC ............ *G06T 7/0012* (2013.01); *G06T 17/10* (2013.01); *G06V 10/806* (2022.01); *G06V 10/809* (2022.01); *G06V 30/2504* (2022.01); *G06T 2207/30068* (2013.01)

(58) Field of Classification Search
USPC ....... 382/100, 103, 128–134, 154, 162, 173, 382/181, 190, 199, 224, 254, 275–276, 382/285–291, 305, 260; 378/4, 21; 715/771; 705/64
See application file for complete search history.

(56) References Cited

U.S. PATENT DOCUMENTS

| | | | |
|---|---|---|---|
| 3,971,950 A | 7/1976 | Evans et al. |
| 4,160,906 A | 7/1979 | Daniels |
| 4,310,766 A | 1/1982 | Finkenzeller et al. |
| 4,496,557 A | 1/1985 | Malen et al. |
| 4,559,641 A | 12/1985 | Caugant et al. |
| 4,706,269 A | 11/1987 | Reina et al. |
| 4,727,565 A | 2/1988 | Ericson |
| 4,744,099 A | 5/1988 | Huettenrauch |
| 4,773,086 A | 9/1988 | Fujita |
| 4,773,087 A | 9/1988 | Plewes |
| 4,819,258 A | 4/1989 | Kleinman et al. |
| 4,821,727 A | 4/1989 | Levene et al. |
| 4,907,156 A | 6/1990 | Doi et al. |
| 4,969,174 A | 11/1990 | Schied |
| 4,989,227 A | 1/1991 | Tirelli et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,099,846 A | 3/1992 | Hardy |
| 5,129,911 A | 7/1992 | Siczek et al. |
| 5,133,020 A | 7/1992 | Giger et al. |
| 5,163,075 A | 11/1992 | Lubinsky |
| 5,164,976 A | 11/1992 | Scheid et al. |
| 5,199,056 A | 3/1993 | Darrah |
| 5,219,351 A | 6/1993 | Teubner |
| 5,240,011 A | 8/1993 | Assa |
| 5,279,309 A | 1/1994 | Taylor et al. |
| 5,280,427 A | 1/1994 | Magnusson |
| 5,289,520 A | 2/1994 | Pellegrino et al. |
| 5,343,390 A | 8/1994 | Doi et al. |
| 5,359,637 A | 10/1994 | Webbe |
| 5,365,562 A | 11/1994 | Toker |
| 5,386,447 A | 1/1995 | Siczek |
| 5,415,169 A | 5/1995 | Siczek et al. |
| 5,426,685 A | 6/1995 | Pellegrino et al. |
| 5,452,367 A | 9/1995 | Bick |
| 5,491,627 A | 2/1996 | Zhang et al. |
| 5,499,097 A | 3/1996 | Ortyn et al. |
| 5,506,877 A | 4/1996 | Niklason et al. |
| 5,526,394 A | 6/1996 | Siczek |
| 5,539,797 A | 7/1996 | Heidsieck et al. |
| 5,553,111 A | 9/1996 | Moore |
| 5,592,562 A | 1/1997 | Rooks |
| 5,594,769 A | 1/1997 | Pellegrino et al. |
| 5,596,200 A | 1/1997 | Sharma |
| 5,598,454 A | 1/1997 | Franetzki |
| 5,609,152 A | 3/1997 | Pellegrino et al. |
| 5,627,869 A | 5/1997 | Andrew et al. |
| 5,642,433 A | 6/1997 | Lee et al. |
| 5,642,441 A | 6/1997 | Riley et al. |
| 5,647,025 A | 7/1997 | Frost et al. |
| 5,657,362 A | 8/1997 | Giger et al. |
| 5,660,185 A | 8/1997 | Shmulewitz et al. |
| 5,668,889 A | 9/1997 | Hara |
| 5,671,288 A | 9/1997 | Wilhelm et al. |
| 5,712,890 A | 1/1998 | Spivey |
| 5,719,952 A | 2/1998 | Rooks |
| 5,735,264 A | 4/1998 | Siczek et al. |
| 5,763,871 A | 6/1998 | Ortyn et al. |
| 5,769,086 A | 6/1998 | Ritchart et al. |
| 5,773,832 A | 6/1998 | Sayed et al. |
| 5,803,912 A | 9/1998 | Siczek et al. |
| 5,818,898 A | 10/1998 | Tsukamoto et al. |
| 5,828,722 A | 10/1998 | Ploetz |
| 5,835,079 A | 11/1998 | Shieh |
| 5,841,124 A | 11/1998 | Ortyn et al. |
| 5,872,828 A | 2/1999 | Niklason et al. |
| 5,875,258 A | 2/1999 | Ortyn et al. |
| 5,878,104 A | 3/1999 | Ploetz |
| 5,878,746 A | 3/1999 | Lemelson et al. |
| 5,896,437 A | 4/1999 | Ploetz |
| 5,941,832 A | 8/1999 | Tumey |
| 5,954,650 A | 9/1999 | Saito |
| 5,986,662 A | 11/1999 | Argiro |
| 6,005,907 A | 12/1999 | Ploetz |
| 6,022,325 A | 2/2000 | Siczek et al. |
| 6,067,079 A | 5/2000 | Shieh |
| 6,075,879 A | 6/2000 | Roehrig et al. |
| 6,091,841 A | 7/2000 | Rogers |
| 6,101,236 A | 8/2000 | Wang et al. |
| 6,102,866 A | 8/2000 | Nields et al. |
| 6,137,527 A | 10/2000 | Abdel-Malek |
| 6,141,398 A | 10/2000 | He |
| 6,149,301 A | 11/2000 | Kautzer et al. |
| 6,175,117 B1 | 1/2001 | Komardin |
| 6,196,715 B1 | 3/2001 | Nambu |
| 6,215,892 B1 | 4/2001 | Douglass et al. |
| 6,216,540 B1 | 4/2001 | Nelson |
| 6,219,059 B1 | 4/2001 | Argiro |
| 6,256,370 B1 | 4/2001 | Yavus |
| 6,233,473 B1 | 5/2001 | Sheperd |
| 6,243,441 B1 | 6/2001 | Zur |
| 6,245,028 B1 | 6/2001 | Furst et al. |
| 6,272,207 B1 | 8/2001 | Tang |
| 6,289,235 B1 | 9/2001 | Webber et al. |
| 6,292,530 B1 | 9/2001 | Yavus |
| 6,293,282 B1 | 9/2001 | Lemelson |
| 6,327,336 B1 | 12/2001 | Gingold et al. |
| 6,327,377 B1 | 12/2001 | Rutenberg et al. |
| 6,341,156 B1 | 1/2002 | Baetz |
| 6,375,352 B1 | 4/2002 | Hewes |
| 6,389,104 B1 | 5/2002 | Bani-Hashemi et al. |
| 6,411,836 B1 | 6/2002 | Patel |
| 6,415,015 B2 | 7/2002 | Nicolas |
| 6,424,332 B1 | 7/2002 | Powell |
| 6,442,288 B1 | 8/2002 | Haerer |
| 6,459,925 B1 | 10/2002 | Nields et al. |
| 6,463,181 B2 | 10/2002 | Duarte |
| 6,468,226 B1 | 10/2002 | McIntyre, IV |
| 6,480,565 B1 | 11/2002 | Ning |
| 6,501,819 B2 | 12/2002 | Unger et al. |
| 6,556,655 B1 | 4/2003 | Chichereau |
| 6,574,304 B1 | 6/2003 | Hsieh |
| 6,597,762 B1 | 7/2003 | Ferrant |

(56) References Cited

U.S. PATENT DOCUMENTS

| | | |
|---|---|---|
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,674 B1 | 10/2003 | Barnes |
| 6,638,235 B2 | 10/2003 | Miller et al. |
| 6,647,092 B2 | 11/2003 | Eberhard |
| 6,650,928 B1 | 11/2003 | Gailly |
| 6,683,934 B1 | 1/2004 | Zhao |
| 6,744,848 B2 | 6/2004 | Stanton |
| 6,748,044 B2 | 6/2004 | Sabol et al. |
| 6,751,285 B2 | 6/2004 | Eberhard |
| 6,758,824 B1 | 7/2004 | Miller et al. |
| 6,813,334 B2 | 11/2004 | Koppe |
| 6,882,700 B2 | 4/2005 | Wang |
| 6,885,724 B2 | 4/2005 | Li |
| 6,901,156 B2 | 5/2005 | Giger et al. |
| 6,912,319 B1 | 5/2005 | Barnes |
| 6,940,943 B2 | 9/2005 | Claus |
| 6,978,040 B2 | 12/2005 | Berestov |
| 6,987,331 B2 | 1/2006 | Koeppe |
| 6,999,554 B2 | 2/2006 | Mertelmeier |
| 7,022,075 B2 | 4/2006 | Grunwald et al. |
| 7,025,725 B2 | 4/2006 | Dione et al. |
| 7,030,861 B1 | 4/2006 | Westerman |
| 7,110,490 B2 | 9/2006 | Eberhard |
| 7,110,502 B2 | 9/2006 | Tsuji |
| 7,117,098 B1 | 10/2006 | Dunlay et al. |
| 7,123,684 B2 | 10/2006 | Jing et al. |
| 7,127,091 B2 | 10/2006 | OpDeBeek |
| 7,142,633 B2 | 11/2006 | Eberhard |
| 7,218,766 B2 | 5/2007 | Eberhard |
| 7,245,694 B2 | 7/2007 | Jing et al. |
| 7,286,634 B2 | 10/2007 | Sommer, Jr. et al. |
| 7,289,825 B2 | 10/2007 | Fors et al. |
| 7,298,881 B2 | 11/2007 | Giger et al. |
| 7,315,607 B2 | 1/2008 | Ramsauer |
| 7,319,735 B2 | 1/2008 | Defreitas et al. |
| 7,323,692 B2 | 1/2008 | Rowlands |
| 7,346,381 B2 | 3/2008 | Okerlund et al. |
| 7,406,150 B2 | 7/2008 | Minyard et al. |
| 7,430,272 B2 | 9/2008 | Jing et al. |
| 7,443,949 B2 | 10/2008 | Defreitas et al. |
| 7,466,795 B2 | 12/2008 | Eberhard et al. |
| 7,577,282 B2 | 8/2009 | Gkanatsios et al. |
| 7,606,801 B2* | 10/2009 | Faitelson ............ G06F 21/604 |
| | | 705/64 |
| 7,616,801 B2 | 11/2009 | Gkanatsios et al. |
| 7,630,533 B2 | 12/2009 | Ruth et al. |
| 7,634,050 B2 | 12/2009 | Muller et al. |
| 7,640,051 B2 | 12/2009 | Krishnan |
| 7,697,660 B2 | 4/2010 | Ning |
| 7,702,142 B2* | 4/2010 | Ren ...................... G06T 11/006 |
| | | 378/68 |
| 7,705,830 B2 | 4/2010 | Westerman et al. |
| 7,760,924 B2* | 7/2010 | Ruth ...................... G06T 15/08 |
| | | 382/128 |
| 7,769,219 B2 | 8/2010 | Zahniser |
| 7,787,936 B2 | 8/2010 | Kressy |
| 7,809,175 B2 | 10/2010 | Roehrig et al. |
| 7,828,733 B2 | 11/2010 | Zhang et al. |
| 7,831,296 B2 | 11/2010 | DeFreitas et al. |
| 7,869,563 B2 | 1/2011 | DeFreitas |
| 7,974,924 B2 | 7/2011 | Holla et al. |
| 7,991,106 B2 | 8/2011 | Ren et al. |
| 8,044,972 B2 | 10/2011 | Hall et al. |
| 8,051,386 B2 | 11/2011 | Rosander et al. |
| 8,126,226 B2 | 2/2012 | Bernard et al. |
| 8,155,421 B2 | 4/2012 | Ren et al. |
| 8,165,365 B2 | 4/2012 | Bernard et al. |
| 8,532,745 B2 | 9/2013 | DeFreitas et al. |
| 8,571,289 B2 | 10/2013 | Ruth |
| 8,594,274 B2 | 11/2013 | Hoernig et al. |
| 8,677,282 B2 | 3/2014 | Cragun et al. |
| 8,712,127 B2 | 4/2014 | Ren et al. |
| 8,897,535 B2 | 11/2014 | Ruth et al. |
| 8,983,156 B2 | 3/2015 | Periaswamy et al. |
| 9,020,579 B2 | 4/2015 | Smith |
| 9,075,903 B2 | 7/2015 | Marshall |
| 9,084,579 B2 | 7/2015 | Ren et al. |
| 9,119,599 B2 | 9/2015 | Itai |
| 9,129,362 B2 | 9/2015 | Jerebko |
| 9,289,183 B2 | 3/2016 | Karssemeijer |
| 9,451,924 B2 | 9/2016 | Bernard |
| 9,456,797 B2 | 10/2016 | Ruth et al. |
| 9,478,028 B2 | 10/2016 | Parthasarathy |
| 9,589,374 B1 | 3/2017 | Gao |
| 9,592,019 B2 | 3/2017 | Sugiyama |
| 9,805,507 B2 | 10/2017 | Chen |
| 9,808,215 B2 | 11/2017 | Ruth et al. |
| 9,811,758 B2 | 11/2017 | Ren et al. |
| 9,901,309 B2 | 2/2018 | DeFreitas et al. |
| 10,008,184 B2 | 6/2018 | Kreeger et al. |
| 10,010,302 B2 | 7/2018 | Ruth et al. |
| 10,092,358 B2 | 10/2018 | DeFreitas |
| 10,111,631 B2 | 10/2018 | Gkanatsios |
| 10,242,490 B2 | 3/2019 | Karssemeijer |
| 10,335,094 B2 | 7/2019 | DeFreitas |
| 10,357,211 B2 | 7/2019 | Smith |
| 10,410,417 B2 | 9/2019 | Chen et al. |
| 10,413,263 B2 | 9/2019 | Ruth et al. |
| 10,444,960 B2 | 10/2019 | Marshall |
| 10,456,213 B2 | 10/2019 | DeFreitas |
| 10,573,276 B2 | 2/2020 | Kreeger et al. |
| 10,575,807 B2 | 3/2020 | Gkanatsios |
| 10,595,954 B2 | 3/2020 | DeFreitas |
| 10,624,598 B2 | 4/2020 | Chen |
| 10,977,863 B2 | 4/2021 | Chen |
| 10,978,026 B2 | 4/2021 | Kreeger |
| 11,419,565 B2 | 8/2022 | Gkanatsios |
| 11,508,340 B2 | 11/2022 | Kreeger |
| 2001/0038681 A1 | 11/2001 | Stanton et al. |
| 2001/0038861 A1 | 11/2001 | Hsu et al. |
| 2002/0012450 A1 | 1/2002 | Tsuji |
| 2002/0050986 A1 | 5/2002 | Inoue |
| 2002/0075997 A1 | 6/2002 | Unger et al. |
| 2002/0113681 A1 | 8/2002 | Byram |
| 2002/0122533 A1 | 9/2002 | Marie et al. |
| 2002/0188466 A1 | 12/2002 | Barrette et al. |
| 2002/0193676 A1 | 12/2002 | Bodicker |
| 2003/0007598 A1 | 1/2003 | Wang |
| 2003/0018272 A1 | 1/2003 | Treado et al. |
| 2003/0026386 A1 | 2/2003 | Tang |
| 2003/0048260 A1 | 3/2003 | Matusis |
| 2003/0073895 A1 | 4/2003 | Nields et al. |
| 2003/0095624 A1 | 5/2003 | Eberhard et al. |
| 2003/0097055 A1 | 5/2003 | Yanof |
| 2003/0128893 A1 | 7/2003 | Castorina |
| 2003/0135115 A1 | 7/2003 | Burdette et al. |
| 2003/0169847 A1 | 9/2003 | Karellas |
| 2003/0194050 A1 | 10/2003 | Eberhard |
| 2003/0194121 A1 | 10/2003 | Eberhard et al. |
| 2003/0195433 A1 | 10/2003 | Turovskiy |
| 2003/0210254 A1 | 11/2003 | Doan |
| 2003/0212327 A1 | 11/2003 | Wang |
| 2003/0215120 A1 | 11/2003 | Uppaluri |
| 2004/0008809 A1 | 1/2004 | Webber |
| 2004/0008900 A1 | 1/2004 | Jabri et al. |
| 2004/0008901 A1 | 1/2004 | Avinash |
| 2004/0036680 A1 | 2/2004 | Davis |
| 2004/0047518 A1 | 3/2004 | Tiana |
| 2004/0052328 A1 | 3/2004 | Saboi |
| 2004/0064037 A1 | 4/2004 | Smith |
| 2004/0066884 A1 | 4/2004 | Claus |
| 2004/0066904 A1 | 4/2004 | Eberhard et al. |
| 2004/0070582 A1 | 4/2004 | Smith et al. |
| 2004/0077938 A1 | 4/2004 | Mark et al. |
| 2004/0081273 A1 | 4/2004 | Ning |
| 2004/0094167 A1 | 5/2004 | Brady |
| 2004/0101095 A1 | 5/2004 | Jing et al. |
| 2004/0109028 A1 | 6/2004 | Stern et al. |
| 2004/0109529 A1 | 6/2004 | Eberhard et al. |
| 2004/0127789 A1 | 7/2004 | Ogawa |
| 2004/0138569 A1 | 7/2004 | Grunwald |
| 2004/0171933 A1 | 9/2004 | Stoller et al. |

(56) References Cited

U.S. PATENT DOCUMENTS

| | | |
|---|---|---|
| 2004/0171986 A1 | 9/2004 | Tremaglio, Jr. et al. |
| 2004/0267157 A1 | 12/2004 | Miller et al. |
| 2005/0047636 A1 | 3/2005 | Gines et al. |
| 2005/0049521 A1 | 3/2005 | Miller et al. |
| 2005/0063509 A1 | 3/2005 | Defreitas et al. |
| 2005/0078797 A1 | 4/2005 | Danielsson et al. |
| 2005/0084060 A1 | 4/2005 | Seppi et al. |
| 2005/0089205 A1 | 4/2005 | Kapur |
| 2005/0105679 A1 | 5/2005 | Wu et al. |
| 2005/0107689 A1 | 5/2005 | Sasano |
| 2005/0111718 A1 | 5/2005 | MacMahon |
| 2005/0113680 A1 | 5/2005 | Ikeda et al. |
| 2005/0113681 A1 | 5/2005 | DeFreitas et al. |
| 2005/0113715 A1 | 5/2005 | Schwindt et al. |
| 2005/0124845 A1 | 6/2005 | Thomadsen et al. |
| 2005/0135555 A1 | 6/2005 | Claus |
| 2005/0135664 A1 | 6/2005 | Kaufhold |
| 2005/0226375 A1 | 10/2005 | Eberhard |
| 2006/0009693 A1 | 1/2006 | Hanover et al. |
| 2006/0018526 A1 | 1/2006 | Avinash |
| 2006/0025680 A1 | 2/2006 | Jeune-Iomme |
| 2006/0030784 A1 | 2/2006 | Miller et al. |
| 2006/0074288 A1 | 4/2006 | Kelly et al. |
| 2006/0098855 A1 | 5/2006 | Gkanatsios et al. |
| 2006/0129062 A1 | 6/2006 | Nicoson et al. |
| 2006/0132508 A1 | 6/2006 | Sadikali |
| 2006/0147099 A1 | 7/2006 | Marshall et al. |
| 2006/0155209 A1 | 7/2006 | Miller et al. |
| 2006/0197753 A1 | 9/2006 | Hotelling |
| 2006/0210131 A1 | 9/2006 | Wheeler |
| 2006/0228012 A1 | 10/2006 | Masuzawa |
| 2006/0238546 A1 | 10/2006 | Handley |
| 2006/0257009 A1 | 11/2006 | Wang |
| 2006/0269040 A1 | 11/2006 | Mertelmeier |
| 2006/0274928 A1 | 12/2006 | Collins et al. |
| 2006/0291618 A1 | 12/2006 | Eberhard et al. |
| 2007/0019846 A1 | 1/2007 | Bullitt et al. |
| 2007/0030949 A1 | 2/2007 | Jing et al. |
| 2007/0036265 A1 | 2/2007 | Jing et al. |
| 2007/0046649 A1 | 3/2007 | Reiner |
| 2007/0052700 A1 | 3/2007 | Wheeler et al. |
| 2007/0076844 A1 | 4/2007 | Defreitas et al. |
| 2007/0114424 A1 | 5/2007 | Danielsson et al. |
| 2007/0118400 A1 | 5/2007 | Morita et al. |
| 2007/0156451 A1 | 7/2007 | Gering |
| 2007/0223651 A1 | 9/2007 | Wagenaar et al. |
| 2007/0225600 A1 | 9/2007 | Weibrecht et al. |
| 2007/0236490 A1 | 10/2007 | Casteele |
| 2007/0242800 A1 | 10/2007 | Jing et al. |
| 2007/0263765 A1 | 11/2007 | Wu |
| 2007/0274585 A1 | 11/2007 | Zhang et al. |
| 2008/0019581 A1 | 1/2008 | Gkanatsios et al. |
| 2008/0043905 A1 | 2/2008 | Hassanpourgol |
| 2008/0045833 A1 | 2/2008 | DeFreitas et al. |
| 2008/0101537 A1 | 5/2008 | Sendai |
| 2008/0114614 A1 | 5/2008 | Mahesh et al. |
| 2008/0125643 A1 | 5/2008 | Huisman |
| 2008/0130979 A1 | 6/2008 | Ren |
| 2008/0139896 A1 | 6/2008 | Baumgart |
| 2008/0152086 A1 | 6/2008 | Hall |
| 2008/0165136 A1 | 7/2008 | Christie et al. |
| 2008/0187095 A1 | 8/2008 | Boone et al. |
| 2008/0198966 A1 | 8/2008 | Hjarn |
| 2008/0221479 A1 | 9/2008 | Ritchie |
| 2008/0229256 A1 | 9/2008 | Shibaike |
| 2008/0240533 A1 | 10/2008 | Piron et al. |
| 2008/0297482 A1 | 12/2008 | Weiss |
| 2009/0003519 A1 | 1/2009 | DeFreitas |
| 2009/0005668 A1 | 1/2009 | West et al. |
| 2009/0005693 A1 | 1/2009 | Brauner |
| 2009/0010384 A1 | 1/2009 | Jing et al. |
| 2009/0034684 A1 | 2/2009 | Bernard |
| 2009/0037821 A1 | 2/2009 | O'Neal et al. |
| 2009/0079705 A1 | 3/2009 | Sizelove et al. |
| 2009/0080594 A1 | 3/2009 | Brooks et al. |
| 2009/0080602 A1 | 3/2009 | Brooks et al. |
| 2009/0080604 A1 | 3/2009 | Shores et al. |
| 2009/0080752 A1 | 3/2009 | Ruth |
| 2009/0080765 A1 | 3/2009 | Bernard et al. |
| 2009/0087067 A1 | 4/2009 | Khorasani |
| 2009/0123052 A1 | 5/2009 | Ruth |
| 2009/0129644 A1 | 5/2009 | Daw et al. |
| 2009/0135997 A1 | 5/2009 | Defreitas et al. |
| 2009/0138280 A1 | 5/2009 | Morita et al. |
| 2009/0143674 A1 | 6/2009 | Nields |
| 2009/0167702 A1 | 7/2009 | Nurmi |
| 2009/0171244 A1 | 7/2009 | Ning |
| 2009/0238424 A1 | 9/2009 | Arakita |
| 2009/0259958 A1 | 10/2009 | Ban |
| 2009/0268865 A1 | 10/2009 | Ren et al. |
| 2009/0278812 A1 | 11/2009 | Yasutake |
| 2009/0296882 A1 | 12/2009 | Gkanatsios et al. |
| 2009/0304147 A1 | 12/2009 | Jing et al. |
| 2010/0034348 A1 | 2/2010 | Yu |
| 2010/0049046 A1 | 2/2010 | Peiffer |
| 2010/0054400 A1 | 3/2010 | Ren et al. |
| 2010/0079405 A1 | 4/2010 | Bernstein |
| 2010/0086188 A1 | 4/2010 | Ruth et al. |
| 2010/0088346 A1 | 4/2010 | Urness et al. |
| 2010/0098214 A1 | 4/2010 | Star-Lack et al. |
| 2010/0105879 A1 | 4/2010 | Katayose et al. |
| 2010/0121178 A1 | 5/2010 | Krishnan |
| 2010/0131294 A1 | 5/2010 | Venon |
| 2010/0131482 A1 | 5/2010 | Linthicum et al. |
| 2010/0135558 A1 | 6/2010 | Ruth et al. |
| 2010/0152570 A1 | 6/2010 | Navab |
| 2010/0166267 A1 | 7/2010 | Zhang |
| 2010/0195882 A1 | 8/2010 | Ren et al. |
| 2010/0208037 A1 | 8/2010 | Sendai |
| 2010/0231522 A1 | 9/2010 | Li |
| 2010/0246909 A1 | 9/2010 | Blum |
| 2010/0259561 A1 | 10/2010 | Forutanpour et al. |
| 2010/0259645 A1 | 10/2010 | Kaplan |
| 2010/0260316 A1 | 10/2010 | Stein et al. |
| 2010/0280375 A1 | 11/2010 | Zhang |
| 2010/0293500 A1 | 11/2010 | Cragun |
| 2011/0018817 A1 | 1/2011 | Kryze |
| 2011/0019891 A1 | 1/2011 | Puong |
| 2011/0054944 A1 | 3/2011 | Sandberg et al. |
| 2011/0069808 A1 | 3/2011 | Defreitas et al. |
| 2011/0069906 A1 | 3/2011 | Park |
| 2011/0087132 A1 | 4/2011 | DeFreitas et al. |
| 2011/0105879 A1 | 5/2011 | Masumoto |
| 2011/0109650 A1 | 5/2011 | Kreeger |
| 2011/0110570 A1 | 5/2011 | Bar-Shalev |
| 2011/0110576 A1 | 5/2011 | Kreeger |
| 2011/0125526 A1 | 5/2011 | Gustafson |
| 2011/0150447 A1 | 6/2011 | Li |
| 2011/0163939 A1 | 7/2011 | Tam et al. |
| 2011/0178389 A1 | 7/2011 | Kumar et al. |
| 2011/0182402 A1 | 7/2011 | Partain |
| 2011/0234630 A1 | 9/2011 | Batman et al. |
| 2011/0237927 A1 | 9/2011 | Brooks et al. |
| 2011/0242092 A1 | 10/2011 | Kashiwagi |
| 2011/0310126 A1 | 12/2011 | Georgiev et al. |
| 2012/0014504 A1 | 1/2012 | Jang |
| 2012/0014578 A1 | 1/2012 | Karssemeijer |
| 2012/0069951 A1 | 3/2012 | Toba |
| 2012/0106698 A1 | 5/2012 | Karim |
| 2012/0131488 A1 | 5/2012 | Karlsson et al. |
| 2012/0133600 A1 | 5/2012 | Marshall |
| 2012/0133601 A1 | 5/2012 | Marshall |
| 2012/0134464 A1 | 5/2012 | Hoernig et al. |
| 2012/0148151 A1 | 6/2012 | Hamada |
| 2012/0189092 A1 | 7/2012 | Jerebko |
| 2012/0194425 A1 | 8/2012 | Buelow |
| 2012/0238870 A1 | 9/2012 | Smith et al. |
| 2012/0293511 A1 | 11/2012 | Mertelmeier |
| 2013/0022165 A1 | 1/2013 | Jang |
| 2013/0044861 A1 | 2/2013 | Muller |
| 2013/0059758 A1 | 3/2013 | Haick |
| 2013/0108138 A1 | 5/2013 | Nakayama |
| 2013/0121569 A1 | 5/2013 | Yadav |
| 2013/0121618 A1 | 5/2013 | Yadav |

(56) References Cited

U.S. PATENT DOCUMENTS

| | | | |
|---|---|---|---|
| 2013/0202168 A1 | 8/2013 | Jerebko | |
| 2013/0259193 A1 | 10/2013 | Packard | |
| 2014/0033126 A1 | 1/2014 | Kreeger | |
| 2014/0035811 A1 | 2/2014 | Guehring | |
| 2014/0064444 A1 | 3/2014 | Oh | |
| 2014/0073913 A1 | 3/2014 | DeFreitas et al. | |
| 2014/0200433 A1 | 7/2014 | Choi | |
| 2014/0219534 A1 | 8/2014 | Wiemker et al. | |
| 2014/0219548 A1 | 8/2014 | Wels | |
| 2014/0327702 A1 | 11/2014 | Kreeger et al. | |
| 2014/0328517 A1 | 11/2014 | Gluncic | |
| 2015/0052471 A1* | 2/2015 | Chen | A61B 6/466 715/771 |
| 2015/0061582 A1 | 4/2015 | Smith | |
| 2015/0238148 A1 | 8/2015 | Georgescu | |
| 2015/0302146 A1 | 10/2015 | Marshall | |
| 2015/0309712 A1 | 10/2015 | Marshall | |
| 2015/0317538 A1 | 11/2015 | Ren et al. | |
| 2015/0331995 A1 | 11/2015 | Zhao | |
| 2016/0000399 A1 | 1/2016 | Halmann et al. | |
| 2016/0022364 A1 | 1/2016 | DeFreitas et al. | |
| 2016/0051215 A1 | 2/2016 | Chen | |
| 2016/0078645 A1 | 3/2016 | Abdurahman | |
| 2016/0140749 A1 | 5/2016 | Erhard | |
| 2016/0228034 A1* | 8/2016 | Gluncic | G06T 7/0012 |
| 2016/0235380 A1 | 8/2016 | Smith | |
| 2016/0367210 A1* | 12/2016 | Gkanatsios | G06T 11/60 |
| 2017/0071562 A1 | 3/2017 | Suzuki | |
| 2017/0262737 A1 | 9/2017 | Rabinovich | |
| 2018/0047211 A1 | 2/2018 | Chen et al. | |
| 2018/0137385 A1 | 5/2018 | Ren | |
| 2018/0144244 A1 | 5/2018 | Masoud | |
| 2018/0256118 A1 | 9/2018 | DeFreitas | |
| 2019/0015173 A1 | 1/2019 | DeFreitas | |
| 2019/0043456 A1 | 2/2019 | Kreeger | |
| 2019/0290221 A1 | 9/2019 | Smith | |
| 2020/0046303 A1 | 2/2020 | DeFreitas | |
| 2020/0093562 A1 | 3/2020 | DeFreitas | |
| 2020/0184262 A1 | 6/2020 | Chui | |
| 2020/0205928 A1 | 7/2020 | DeFreitas | |
| 2020/0253573 A1 | 8/2020 | Gkanatsios | |
| 2020/0345320 A1 | 11/2020 | Chen | |
| 2020/0390404 A1 | 12/2020 | DeFreitas | |
| 2021/0000553 A1 | 1/2021 | St. Pierre | |
| 2021/0100518 A1 | 4/2021 | Chui | |
| 2021/0100626 A1 | 4/2021 | St. Pierre | |
| 2021/0113167 A1 | 4/2021 | Chui | |
| 2021/0118199 A1 | 4/2021 | Chui | |
| 2022/0005277 A1 | 1/2022 | Chen | |
| 2022/0013089 A1 | 1/2022 | Kreeger | |
| 2022/0386969 A1 | 12/2022 | Smith | |
| 2023/0053489 A1 | 2/2023 | Kreeger | |
| 2023/0054121 A1 | 2/2023 | Chui | |
| 2023/0056692 A1 | 2/2023 | Gkanatsios | |
| 2023/0082494 A1 | 3/2023 | Chui | |
| 2023/0125385 A1 | 4/2023 | Solis | |
| 2023/0225821 A1 | 7/2023 | DeFreitas | |

FOREIGN PATENT DOCUMENTS

| | | |
|---|---|---|
| CN | 101066212 A | 11/2007 |
| CN | 202161328 | 3/2012 |
| CN | 102429678 | 5/2012 |
| CN | 107440730 | 12/2017 |
| CN | 112561908 A | 3/2021 |
| DE | 102010009295 | 8/2011 |
| DE | 102011087127 | 5/2013 |
| EP | 775467 | 5/1997 |
| EP | 982001 | 3/2000 |
| EP | 1428473 | 6/2004 |
| EP | 2236085 | 6/2010 |
| EP | 2215600 | 8/2010 |
| EP | 2301432 | 3/2011 |
| EP | 2491863 | 8/2012 |
| EP | 1986548 | 1/2013 |
| EP | 2656789 | 10/2013 |
| EP | 2823464 | 1/2015 |
| EP | 2823765 | 1/2015 |
| EP | 3060132 | 4/2019 |
| JP | H09-198490 | 7/1997 |
| JP | H09-238934 | 9/1997 |
| JP | H10-33523 | 2/1998 |
| JP | 2000-200340 | 7/2000 |
| JP | 2002-109510 | 4/2002 |
| JP | 2002-282248 | 10/2002 |
| JP | 2003-189179 | 7/2003 |
| JP | 2003-199737 | 7/2003 |
| JP | 2003-531516 | 10/2003 |
| JP | 2004254742 | 9/2004 |
| JP | 2006-519634 | 8/2006 |
| JP | 2006-312026 | 11/2006 |
| JP | 2007-130487 | 5/2007 |
| JP | 2007-330334 | 12/2007 |
| JP | 2007-536968 | 12/2007 |
| JP | 2008-068032 | 3/2008 |
| JP | 2009-034503 | 2/2009 |
| JP | 2009-522005 | 6/2009 |
| JP | 2009-526618 | 7/2009 |
| JP | 2009-207545 | 9/2009 |
| JP | 2010-137004 | 6/2010 |
| JP | 2011-110175 A | 6/2011 |
| JP | 2012-011255 | 1/2012 |
| JP | 2012-501750 | 1/2012 |
| JP | 2012-061196 | 3/2012 |
| JP | 2013-244211 | 12/2013 |
| JP | 2014-507250 | 3/2014 |
| JP | 2014-534042 | 12/2014 |
| JP | 2015-506794 | 3/2015 |
| JP | 2015-144632 A | 8/2015 |
| JP | 2016-198197 | 12/2015 |
| KR | 10-2015-0010515 | 1/2015 |
| KR | 10-2017-0062839 | 6/2017 |
| WO | 90/05485 | 5/1990 |
| WO | 93/17620 | 9/1993 |
| WO | 94/06352 | 3/1994 |
| WO | 1997/00649 | 1/1997 |
| WO | 1998/16903 | 4/1998 |
| WO | 00/51484 | 9/2000 |
| WO | 2003/020114 | 3/2003 |
| WO | 2005051197 | 6/2005 |
| WO | 2005/110230 | 11/2005 |
| WO | 2005110230 | 11/2005 |
| WO | 2005/112767 | 12/2005 |
| WO | 2005112767 | 12/2005 |
| WO | 2006/055830 | 5/2006 |
| WO | 2006/058160 | 6/2006 |
| WO | 2007/095330 | 8/2007 |
| WO | 08/014670 | 2/2008 |
| WO | 2008047270 | 4/2008 |
| WO | 2008/054436 | 5/2008 |
| WO | 2009/026587 | 2/2009 |
| WO | 2010/028208 | 3/2010 |
| WO | 2010059920 | 5/2010 |
| WO | 2011008239 | 1/2011 |
| WO | 2011/043838 | 4/2011 |
| WO | 2011065950 | 6/2011 |
| WO | 2011073864 | 6/2011 |
| WO | 2011091300 | 7/2011 |
| WO | 2012/001572 | 1/2012 |
| WO | 2012/068373 | 5/2012 |
| WO | 2012063653 | 5/2012 |
| WO | 2012/112627 | 8/2012 |
| WO | 2012/122399 | 9/2012 |
| WO | 2013/001439 | 1/2013 |
| WO | 2013/035026 | 3/2013 |
| WO | 2013/078476 | 5/2013 |
| WO | 2013/123091 | 8/2013 |
| WO | 2014/080215 | 5/2014 |
| WO | 2014/149554 | 9/2014 |
| WO | 2014/207080 | 12/2014 |
| WO | 2015/061582 | 4/2015 |
| WO | 2015/066650 | 5/2015 |
| WO | 2015/130916 | 9/2015 |

(56) References Cited

FOREIGN PATENT DOCUMENTS

| WO | 2016/103094 | 6/2016 |
|----|-------------|--------|
| WO | 2016/184746 | 11/2016 |
| WO | 2018/183548 | 10/2018 |
| WO | 2018/183549 | 10/2018 |
| WO | 2018/183550 | 10/2018 |
| WO | 2018/236565 | 12/2018 |
| WO | 2021/021329 | 2/2021 |

OTHER PUBLICATIONS

Williams, Mark B. et al., "Optimization of exposure parameters in full field digital mammography", Medical Physics 35, 2414 (May 20, 2008); doi: 10.1118/1.2912177, pp. 2414-2423.

Elbakri, Idris A. et al., "Automatic exposure control for a slot scannong full field digital mammagraphy system", Med. Phys. 2005; Sep. 32(9):2763-2770, Abstract only.

Feng, Steve Si Jia, et al., "Clinical digital breast tomosynthesis system: Dosimetric Characterization", Radiology, Apr. 2012, 263(1); pp. 35-42.

"Filtered Back Projection", (Nygren), published May 8, 2007, URL: http://web.archive.org/web/19991010131715/http://www.owlnet.rice.edu/~elec539/Projects97/cult/node2.html, 2 pgs.

"Supersonic to feature Aixplorer Ultimate at ECR", AuntiMinnie.com, 3 pages (Feb. 2018).

Al Sallab et al., "Self Learning Machines Using Deep Networks", Soft Computing and Pattern Recognition (SoCPaR), 2011 Int'l. Conference of IEEE, Oct. 14, 2011, pp. 21-26.

Berg, WA et al., "Combined screening with ultrasound and mammography vs mammography alone in women at elevated risk of breast cancer", JAMA 299:2151-2163, 2008.

Burbank, Fred, "Stereotactic Breast Biopsy: Its History, Its Present, and Its Future", published in 1996 at the Southeastern Surgical Congress, 24 pages.

Bushberg, Jerrold et al., "The Essential Physics of Medical Imaging", 3rd ed., In: "The Essential Physics of Medical Imaging, Third Edition", Dec. 28, 2011, Lippincott & Wilkins, Philadelphia, PA, USA, XP05579051, pp. 270-272.

Caroline, B.E et al., "Computer aided detection of masses in digital breast tomosynthesis: A review", 2012 International Conference on Emerging Trends in Science, Engineering and Technology (INCOSET), Tiruchirappalli, 2012, pp. 186-191.

Carton, AK, et al., "Dual-energy contrast-enhanced digital breast tomosynthesis—a feasibility study", Br J Radiol. Apr. 2010;83 (988):344-50.

Chan, Heang-Ping et al., "ROC Study of the effect of stereoscopic imaging on assessment of breast lesions," Medical Physics, vol. 32, No. 4, Apr. 2005, 1001-1009.

Chen, SC, et al., "Initial clinical experience with contrast-enhanced digital breast tomosynthesis", Acad Radio. Feb. 2007 14(2):229-38.

Diekmann, Felix., et al., "Digital mammography using iodine-based contrast media: initial clinical experience with dynamic contrast medium enhancement", Invest Radiol 2005; 40:397-404.

Dromain C., et al., "Contrast enhanced spectral mammography: a multi-reader study", RSNA 2010, 96th Scientific Assembly and Scientific Meeting.

Dromain, C., et al., "Contrast-enhanced digital mammography", Eur J Radiol. 2009; 69:34-42.

Dromain, Clarisse et al., "Dual-energy contrast-enhanced digital mammography: initial clinical results", European Radiology, Sep. 14, 2010, vol. 21, pp. 565-574.

E. Shaw de Paredes et al., "Interventional Breast Procedure", published Sep./Oct. 1998 in Curr Probl Diagn Radiol, pp. 138-184. (D15 in oppo).

EFilm Mobile HD by Merge Healthcare, web site: http://itunes.apple.com/bw/app/efilm-mobile-hd/id405261243?mt=8, accessed on Nov. 3, 2011 (2 pages).

EFilm Solutions, eFilm Workstation (tm) 3.4, website: http://estore.merge.com/na/estore/content.aspx?productID=405, accessed on Nov. 3, 2011 (2 pages).

Ertas, M. et al., "2D versus 3D total variation minimization in digital breast tomosynthesis", 2015 IEEE International Conference on Imaging Systems and Techniques (IST), Macau, 2015, pp. 1-4.

Fischer Imaging Corp, Mammotest Plus manual on minimally invasive breast biopsy system, 2002, 8 pages.

Fischer Imaging Corporation, Installation Manual, MammoTest Family of Breast Biopsy Systems, 86683G, 86684G, P-55957-IM, Issue 1, Revision 3, Jul. 2005, 98 pages.

Fischer Imaging Corporation, Operator Manual, MammoTest Family of Breast Biopsy Systems, 86683G, 86684G, P-55956-OM, Issue 1, Revision 6, Sep. 2005, 258 pages.

Freiherr, G., "Breast tomosynthesis trials show promise", Diagnostic Imaging—San Francisco 2005, V27; N4:42-48.

Georgian-Smith, Dianne, et al., "Stereotactic Biopsy of the Breast Using an Upright Unit, a Vacuum-Suction Needle, and a Lateral Arm-Support System", 2001, at the American Roentgen Ray Society meeting, 8 pages.

Ghiassi, M. et al., "A Dynamic Architecture for Artificial Networks", Neurocomputing, vol. 63, Aug. 20, 2004, pp. 397-413.

Giger et al. "Development of a smart workstation for use in mammography", in Proceedings of SPIE, vol. 1445 (1991), pp. 101103; 4 pages.

Giger et al., "An Intelligent Workstation for Computer-aided Diagnosis", in RadioGraphics, May 1993, 13:3 pp. 647-656; 10 pages.

Hologic, "Lorad StereoLoc II" Operator's Manual 9-500-0261, Rev. 005, 2004, 78 pgs.

Hologic, Inc., 510(k) Summary, prepared Nov. 28, 2010, for Affirm Breast Biopsy Guidance System Special 510(k) Premarket Notification, 5 pages.

Hologic, Inc., 510(k) Summary, prepared Aug. 14, 2012, for Affirm Breast Biopsy Guidance System Special 510(k) Premarket Notification, 5 pages.

ICRP Publication 60: 1990 Recommendations of the International Commission on Radiological Protection, 12 pages.

Jochelson, M., et al., "Bilateral Dual Energy contrast-enhanced digital mammography: Initial Experience", RSNA 2010, 96th Scientific Assembly and Scientific Meeting, 1 page.

Jong, RA, et al., Contrast-enhanced digital mammography: initial clinical experience. Radiology 2003; 228:842-850.

Koechli, Ossi R., "Available Sterotactic Systems for Breast Biopsy", Renzo Brun del Re (Ed.), Minimally Invasive Breast Biopsies, Recent Results in Cancer Research 173:105-113; Springer-Verlag, 2009.

Kopans, et al. Will tomosynthesis replace conventional mammography? Plenary Session SFN08: RSNA 2005.

Lehman, CD, et al. MRI evaluation of the contralateral breast in women with recently diagnosed breast cancer. N Engl J Med 2007; 356:1295-1303.

Lewin,JM, et al., Dual-energy contrast-enhanced digital subtraction mammography: feasibility. Radiology 2003; 229:261-268.

Lilja, Mikko, "Fast and accurate voxel projection technique in free-form cone-beam geometry with application to algebraic reconstruction," Applies Sciences on Biomedical and Communication Technologies, 2008, Isabel '08, first international symposium on, IEEE, Piscataway, NJ, Oct. 25, 2008.

Lindfors, KK, et al., Dedicated breast CT: initial clinical experience. Radiology 2008; 246(3): 725-733.

Niklason, L., et al., Digital tomosynthesis in breast imaging. Radiology. Nov. 1997; 205(2):399-406.

Pathmanathan et al., "Predicting tumour location by simulating large deformations of the breast using a 3D finite element model and nonlinear elasticity", Medical Image Computing and Computer-Assisted Intervention, pp. 217-224, vol. 3217 (2004).

PCT International Preliminary Report on Patentability in International Application PCT/US2018/024911, dated Oct. 10, 2019, 8 pages.

PCT International Search Report and Written Opinion in International Application PCT/US2018/024911, dated Jul. 2, 2018, 10 pages.

Pediconi, "Color-coded automated signal intensity-curve for detection and characterization of breast lesions: Preliminary evaluation of new software for MR-based breast imaging," International Congress Series 1281 (2005) 1081-1086.

(56) References Cited

OTHER PUBLICATIONS

Poplack, SP, et al., Digital breast tomosynthesis: initial experience in 98 women with abnormal digital screening mammography. AJR Am J Roentgenology Sep. 2007 189(3):616-23.

Prionas, ND, et al., Contrast-enhanced dedicated breast CT: initial clinical experience. Radiology. Sep. 2010 256(3):714-723.

Rafferty, E. et al., "Assessing Radiologist Performance Using Combined Full-Field Digital Mammography and Breast Tomosynthesis Versus Full-Field Digital Mammography Alone: Results" . . . presented at 2007 Radiological Society of North America meeting, Chicago IL.

Reynolds, April, "Stereotactic Breast Biopsy: A Review", Radiologic Technology, vol. 80, No. 5, Jun. 1, 2009, pp. 447M-464M, XP055790574.

Sakic et al., "Mammogram synthesis using a 3D simulation. I. breast tissue model and image acquisition simulation" Medical Physics. 29, pp. 2131-2139 (2002).

Samani, A. et al., "Biomechanical 3-D Finite Element Modeling of the Human Breast Using MRI Data", 2001, IEEE Transactions on Medical Imaging, vol. 20, No. 4, pp. 271-279.

Shrading, Simone et al., "Digital Breast Tomosynthesis-guided Vacuum-assisted Breast Biopsy: Initial Experiences and Comparison with Prone Stereotactic Vacuum-assisted Biopsy", the Department of Diagnostic and Interventional Radiology, Univ. of Aachen, Germany, published Nov. 12, 2014, 10 pgs.

Smith, A., "Full field breast tomosynthesis", Radiol Manage. Sep.-Oct. 2005; 27(5):25-31.

Van Schie, Guido, et al., "Generating Synthetic Mammograms from Reconstructed Tomosynthesis Volumes", IEEE Transactions on Medical Imaging, vol. 32, No. 12, Dec. 2013, 2322-2331.

Van Schie, Guido, et al., "Mass detection in reconstructed digital breast tomosynthesis volumes with a computer-aided detection system trained on 2D mammograms", Med. Phys. 40(4), Apr. 2013, 41902-1-41902-11.

Weidner N, et al., "Tumor angiogenesis and metastasis: correlation in invasive breast carcinoma", New England Journal of Medicine 1991; 324:1-8.

Weidner, N, "The importance of tumor angiogenesis: the evidence continues to grow", Am J Clin Pathol. Nov. 2004 122(5):696-703.

Wodajo, Felasfa, MD, "Now Playing: Radiology Images from Your Hospital PACS on your iPad," Mar. 17, 2010; web site: http://www.imedicalapps.com/2010/03/now-playing-radiology-images-from-your-hospital-pacs-on-your-ipad/, accessed on Nov. 3, 2011 (3 pages).

Yin, H.M., et al., "Image Parser: a tool for finite element generation from three-dimensional medical images", BioMedical Engineering Online. 3:31, pp. 1-9, Oct. 1, 2004.

Diekmann, Felix et al., "Thick Slices from Tomosynthesis Data Sets: Phantom Study for the Evaluation of Different Algorithms", Journal of Digital Imaging, Springer, vol. 22, No. 5, Oct. 23, 2007, pp. 519-526.

Conner, Peter, "Breast Response to Menopausal Hormone Therapy—Aspects on Proliferation, apoptosis and Mammographic Density", 2007 Annals of Medicine, 39;1, 28-41.

Glick, Stephen J., "Breast CT", Annual Rev. Biomed. Eng., 2007, 9;501-26.

Metheany, Kathrine G. et al., "Characterizing anatomical variability in breast CT images", Oct. 2008, Med. Phys. 35 (10); 4685-4694.

Dromain, Clarisse, et al., "Evaluation of tumor angiogenesis of breast carcinoma using contrast-enhanced digital mammography", AJR: 187, Nov. 2006, 16 pages.

Zhao, Bo, et al., "Imaging performance of an amorphous selenium digital mammography detector in a breast tomosynthesis system", May 2008, Med. Phys 35(5); 1978-1987.

Mahesh, Mahadevappa, "AAPM/RSNA Physics Tutorial for Residents—Digital Mammography: An Overview", Nov.-Dec. 2004, vol. 24, No. 6, 1747-1760.

Zhang, Yiheng et al., "A comparative study of limited-angle cone-beam reconstruction methods for breast tomosynthesis", Med Phys., Oct. 2006, 33(10): 3781-3795.

Sechopoulos, et al., "Glandular radiation dose in tomosynthesis of the breast using tungsten targets", Journal of Applied Clinical Medical Physics, vol. 8, No. 4, Fall 2008, 161-171.

Wen, Junhai et al., "A study on truncated cone-beam sampling strategies for 3D mammography", 2004, IEEE, 3200-3204.

Ijaz, Umer Zeeshan, et al., "Mammography phantom studies using 3D electrical impedance tomography with numerical forward solver", Frontiers in the Convergence of Bioscience and Information Technologies 2007, 379-383.

Kao, Tzu-Jen et al., "Regional admittivity spectra with tomosynthesis images for breast cancer detection", Proc. of the 29th Annual Int'l. Conf. of the IEEE EMBS, Aug. 23-26, 2007, 4142-4145.

Varjonen, Mari, "Three-Dimensional Digital Breast Tomosynthesis in the Early Diagnosis and Detection of Breast Cancer", IWDM 2006, LNCS 4046, 152-159.

Taghibakhsh, F. et al., "High dynamic range 2-TFT amplified pixel sensor architecture for digital mammography tomosynthesis", IET Circuits Devices Syst., 2007, 1(10, pp. 87-92.

Chan, Heang-Ping et al., "Computer-aided detection system for breast masses on digital tomosynthesis mammograms: Preliminary Experience", Radiology, Dec. 2005, 1075-1080.

Duan, Xiaoman et al., "Matching corresponding regions of interest on cranio-caudal and medio-lateral oblique view mammograms", IEEE Access, vol. 7, Mar. 25, 2019, pp. 31586-31597, XP011715754, DOI: 10.1109/Access.2019.2902854, retrieved on Mar. 20, 2019, abstract.

Samulski, Maurice et al., "Optimizing case-based detection performance in a multiview CAD system for mammography", IEEE Transactions on Medical Imaging, vol. 30, No. 4, Apr. 1, 2011, pp. 1001-1009, XP011352387, ISSN: 0278-0062, DOI: 10.1109/TMI.2011.2105886, abstract.

Nikunjc, Oza et al., Dietterich, T.G., Ed., "Ensemble methods in machine learning", Jan. 1, 2005, Multiple Classifier Systems, Lecture Notes in Computer Science; LNCS, Springer-Verlag Berlin/Heidelberg, pp. 1-15, abstract.

\* cited by examiner

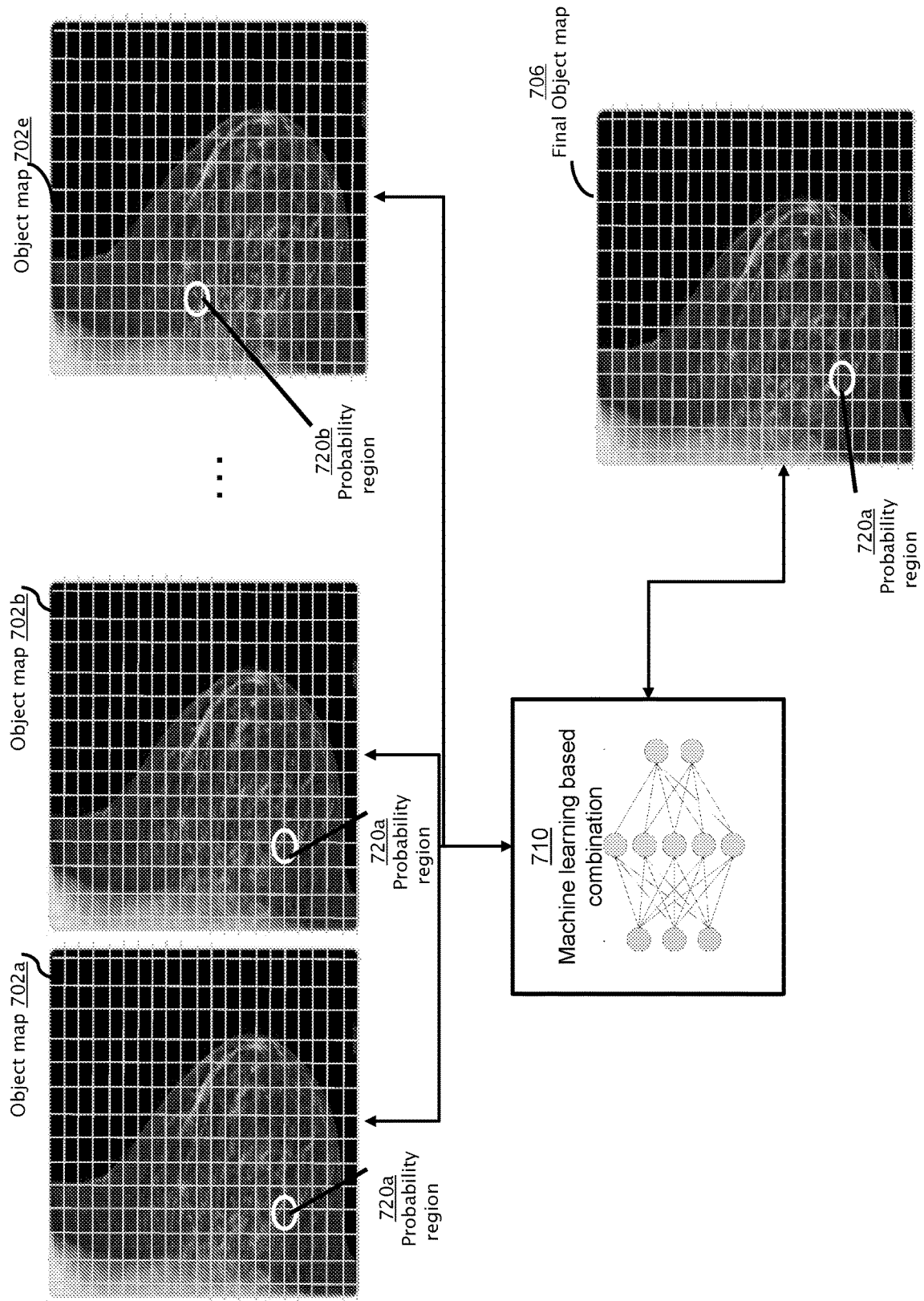

SYSTEM AND METHOD FOR HIERARCHICAL MULTI-LEVEL FEATURE IMAGE SYNTHESIS AND REPRESENTATION

CROSS-REFERENCE TO RELATED APPLICATIONS

This application is a continuation application of U.S. patent application Ser. No. 16/497,764, filed Sep. 25, 2019, which application is a National Phase entry under 35 U.S.C. § 371 of International Patent Application No. PCT/US2018/024911, having an international filing date of Mar. 28, 2018, which claims the benefit under 35 U.S.C. § 119 to U.S. Provisional Patent Application Ser. No. 62/478,977, filed Mar. 30, 2017, the entire disclosures of which are hereby incorporated herein by reference.

FIELD

The presently disclosed inventions relate generally to breast imaging techniques such as tomosynthesis, and more specifically to systems and methods for obtaining, processing, synthesizing, storing and displaying a breast imaging data set or a subset thereof. In particular, the present disclosure relates to creating a high-dimensional grid by decomposing high-dimensional data to lower-dimensional data in order to identify objects to display in one or more synthesized images.

BACKGROUND

Mammography has long been used to screen for breast cancer and other abnormalities. Traditionally, mammograms have been formed on x-ray film. More recently, flat panel digital imagers have been introduced that acquire a mammogram in digital form, and thereby facilitate analysis and storage of the acquired image data, and to also provide other benefits. Further, substantial attention and technological development have been dedicated to obtaining three-dimensional images of the breast using methods such as breast tomosynthesis. In contrast to the 2D images generated by legacy mammography systems, breast tomosynthesis systems construct a 3D image volume from a series of 2D projection images, each projection image obtained at a different angular displacement of an x-ray source relative to the image detector as the x-ray source is scanned over the detector. The constructed 3D image volume is typically presented as a plurality of slices of image data, the slices being mathematically reconstructed on planes typically parallel to the imaging detector. The reconstructed tomosynthesis slices reduce or eliminate the problems caused by tissue overlap and structure noise present in single slice, two-dimensional mammography imaging, by permitting a user (e.g., a radiologist or other medical professional) to scroll through the image slices to view only the structures in that slice.

Imaging systems such as tomosynthesis systems have recently been developed for breast cancer screening and diagnosis. In particular, Hologic, Inc. (www.hologic.com) has developed a fused, multimode mammography/tomosynthesis system that acquires one or both types of mammogram and tomosynthesis images, either while the breast remains immobilized or in different compressions of the breast. Other companies have introduced systems that include tomosynthesis imaging; e.g., which do not include the ability to also acquire a mammogram in the same compression.

Examples of systems and methods that leverage existing medical expertise in order to facilitate, optionally, the transition to tomosynthesis technology are described in U.S. Pat. No. 7,760,924, which is hereby incorporated by reference in its entirety. In particular, U.S. Pat. No. 7,760,924 describes a method of generating a synthesized 2D image, which may optionally be displayed along with tomosynthesis projection or reconstructed images, in order to assist in screening and diagnosis.

The 2D synthesized image is designed to provide a concise representation of the 3D reconstruction slices, including any clinically important and meaningful information, such as abnormal lesions and normal breast structures, while representing in relevant part a traditional 2D image. There are many different types of lesions and breast structures, which may be defined as different types of image objects having different characteristics. For any given image object visible in the 3D volume data, it is important to maintain and enhance the image characteristics (e.g., microcalcifications, architectural distortions, etc.), as much as possible, onto the 2D synthesized image. To achieve the enhancement of the targeted image object, it is critical to accurately identify and represent the image object present in the 3D tomosynthesis data.

SUMMARY

In one embodiment of the disclosed inventions, a method for processing breast tissue image data includes obtaining image data of a patient's breast tissue, and processing the image data to generate a set of image slices that collectively depict the patient's breast tissue. One or more filters associated with a plurality of multi-level feature modules are then applied to each image slice, the multi-level feature modules being configured to and recognize at least one assigned feature of a high-dimensional object that may be present in the patient's breast tissue, wherein the method further includes at each multi-level feature module, generating a feature map depicting regions (if any) of the respective image slice having the at least one assigned feature. The generated feature maps are then combined into an object map, preferably by using a learning library-based combiner, wherein the object map indicates a probability that the respective high-dimensional object is present at a particular location of the image slice. The method may further include creating a 2D synthesized image identifying one or more high-dimensional objects based at least in part on object maps generated for a plurality of image slices.

These and other aspects and embodiments of the disclosed inventions are described in more detail below, in conjunction with the accompanying figures.

BRIEF DESCRIPTION OF THE FIGURES

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

FIGS. 7A and 7B illustrate exemplary combination techniques to combine data to form the object maps.

DETAILED DESCRIPTION OF THE ILLUSTRATED EMBODIMENTS

Figure 1:
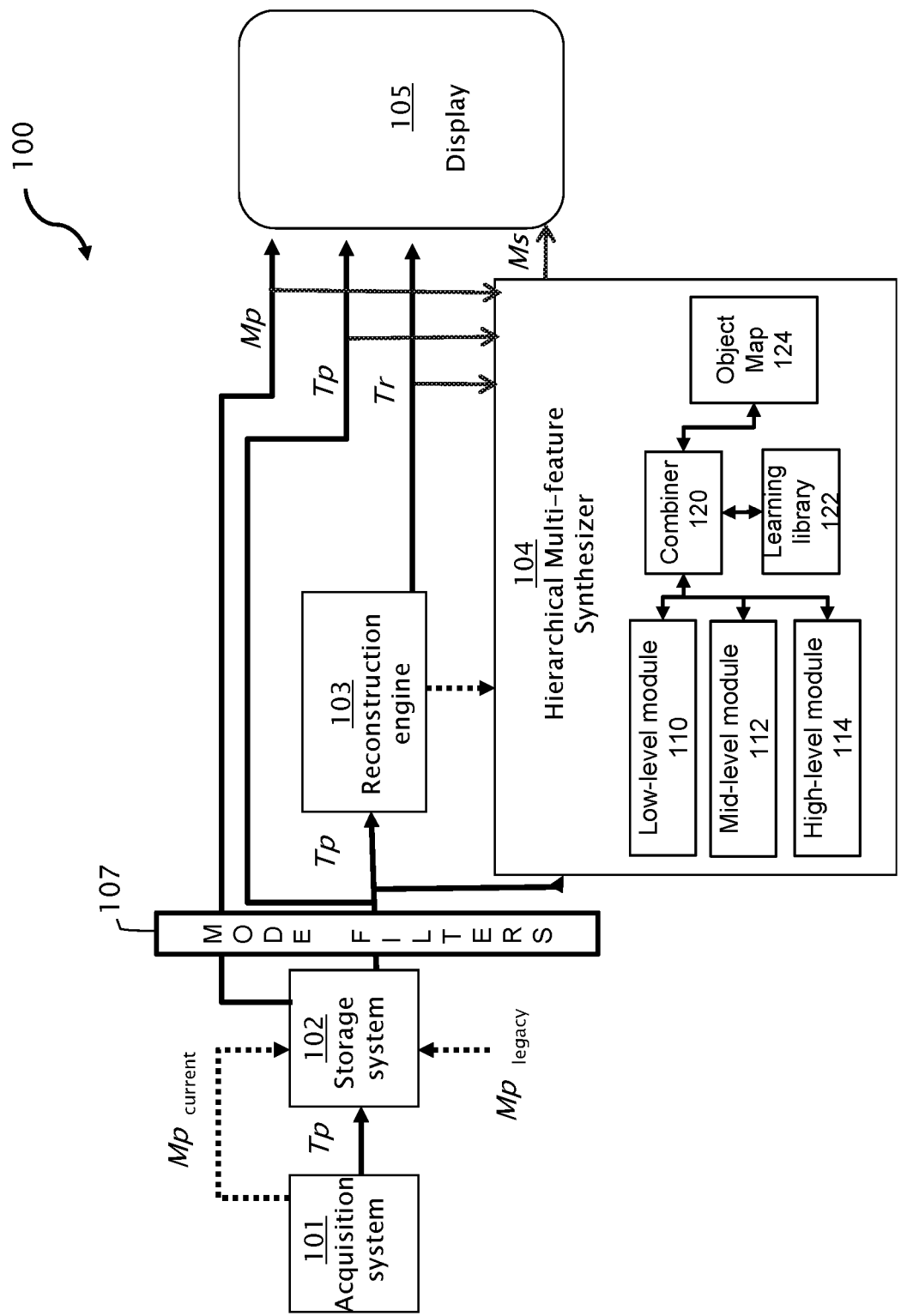
FIG. 1 is a block diagram illustrating the flow of data through an exemplary breast image acquisition and processing system in accordance with embodiments of the disclosed inventions.

All numeric values are herein assumed to be modified by the terms "about" or "approximately," whether or not explicitly indicated, wherein the terms "about" and "approximately" generally refer to a range of numbers that one of skill in the art would consider equivalent to the recited value (i.e., having the same function or result). In some instances, the terms "about" and "approximately" may include numbers that are rounded to the nearest significant figure. The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. In describing the depicted embodiments of the disclosed inventions illustrated in the accompanying figures, specific terminology is employed for the sake of clarity and ease of description. However, the disclosure of this patent specification is not intended to be limited to the specific terminology so selected, and it is to be understood that each specific element includes all technical equivalents that operate in a similar manner. It is to be further understood that the various elements and/or features of different illustrative embodiments may be combined with each other and/or substituted for each other wherever possible within the scope of this disclosure and the appended claims.

Various embodiments of the disclosed inventions are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the disclosed inventions, which is defined only by the appended claims and their equivalents. In addition, an illustrated embodiment of the disclosed inventions needs not have all the aspects or advantages shown. For example, an aspect or an advantage described in conjunction with a particular embodiment of the disclosed inventions is not necessarily limited to that embodiment and can be practiced in any other embodiments even if not so illustrated.

For the following defined terms and abbreviations, these definitions shall be applied throughout this patent specification and the accompanying claims, unless a different definition is given in the claims or elsewhere in this specification:

An "acquired image" refers to an image generated while visualizing a patient's tissue. Acquired images can be generated by radiation from a radiation source impacting on a radiation detector disposed on opposite sides of a patient's tissue, as in a conventional mammogram.

A "reconstructed image" refers to an image generated from data derived from a plurality of acquired images. A reconstructed image simulates an acquired image not included in the plurality of acquired images.

A "synthesized image" refers to an artificial image generated from data derived from a plurality of acquired and/or reconstructed images. A synthesized image includes elements (e.g., objects and regions) from the acquired and/or reconstructed images, but does not necessarily correspond to an image that can be acquired during visualization. Synthesized images are constructed analysis tools.

An "Mp" image is a conventional mammogram or contrast enhanced mammogram, which are two-dimensional (2D) projection images of a breast, and encompasses both a digital image as acquired by a flat panel detector or another imaging device, and the image after conventional processing to prepare it for display (e.g., to a health professional), storage (e.g., in the PACS system of a hospital), and/or other use.

A "Tp" image is an image that is similarly two-dimensional (2D), but is acquired at a respective tomosynthesis angle between the breast and the origin of the imaging x rays (typically the focal spot of an x-ray tube), and encompasses the image as acquired, as well as the image data after being processed for display, storage, and/or other use.

A "Tr" image is type (or subset) of a reconstructed image that is reconstructed from tomosynthesis projection images Tp, for example, in the manner described in one or more of U.S. Pat. Nos. 7,577,282, 7,606,801, 7,760,924, and 8,571, 289, the disclosures of which are fully incorporated by reference herein in their entirety, wherein a Tr image represents a slice of the breast as it would appear in a projection x ray image of that slice at any desired angle, not only at an angle used for acquiring Tp or Mp images.

An "Ms" image is a type (or subset) of a synthesized image, in particular, a synthesized 2D projection image that simulates mammography images, such as a craniocaudal (CC) or mediolateral oblique (MLO) images, and is constructed using tomosynthesis projection images Tp, tomosynthesis reconstructed images Tr, or a combination thereof. Ms images may be provided for display to a health professional or for storage in the PACS system of a hospital or another institution. Examples of methods that may be used to generate Ms images are described in the above-incorporated U.S. Pat. Nos. 7,760,924 and 8,571,289.

It should be appreciated that Tp, Tr, Ms and Mp image data encompasses information, in whatever form, that is sufficient to describe the respective image for display, further processing, or storage. The respective Mp, Ms. Tp and Tr images are typically provided in digital form prior to being displayed, with each image being defined by information that identifies the properties of each pixel in a two-dimensional array of pixels. The pixel values typically relate to respective measured, estimated, or computed responses to X-rays of corresponding volumes in the breast, i.e., voxels or columns of tissue. In a preferred embodiment, the geometry of the tomosynthesis images (Tr and Tp) and mammography images (Ms and Mp) are matched to a common coordinate system, as described in U.S. Pat. No. 7,702,142. Unless otherwise specified, such coordinate system matching is assumed to be implemented with respect to the embodiments described in the ensuing detailed description of this patent specification.

The terms "generating an image" and "transmitting an image" respectively refer to generating and transmitting information that is sufficient to describe the image for display. The generated and transmitted information is typically digital information.

In order to ensure that a synthesized 2D image displayed to an end-user (e.g., an Ms image) includes the most clinically relevant information, it is necessary to detect and identify three-dimensional (3D) objects, such as malignant breast mass, tumors, etc., within the breast tissue. This information may be used to create a high-dimensional grid, e.g., a 3D grid, that helps create a more accurate and enhanced rendering of the most important features in the synthesized 2D image. The present disclosure describes one approach for creating a 3D grid by decomposing high-dimensional objects (i.e., 3D or higher) into lower-dimensional image patterns (2D images). When these 2D image patterns are detected in a tomosynthesis stack of images, they may be combined using a learning library that determines a location and morphology of the corresponding 3D object within the patient's breast tissue. This information regarding the presence of the respective 3D object(s) enables the system to render a more accurate synthesized 2D image to an end-user.

FIG. 1 illustrates the flow of data in an exemplary image generation and display system 100, which incorporates each of synthesized image generation, object identification, and display technology. It should be understood that, while FIG. 1 illustrates a particular embodiment of a flow diagram with certain processes taking place in a particular serial order or in parallel, the claims and various other embodiments described herein are not limited to the performance of the image processing steps in any particular order, unless so specified.

More particularly, the image generation and display system 100 includes an image acquisition system 101 that acquires tomosynthesis image data for generating Tp images of a patient's breasts, using the respective three-dimensional and/or tomosynthesis acquisition methods of any of the currently available systems. If the acquisition system is a combined tomosynthesis/mammography system, Mp images may also be generated. Some dedicated tomosynthesis systems or combined tomosynthesis/mammography systems may be adapted to accept and store legacy mammogram images, (indicated by a dashed line and legend "$MP_{legacy}$" in FIG. 1) in a storage device 102, which is preferably a DICOM-compliant Picture Archiving and Communication System (PACS) storage device. Following acquisition, the tomosynthesis projection images Tp may also be transmitted to the storage device 102 (as shown in FIG. 1). The storage device 102 may further store a library of known 3D objects that may be used to identify significant 3D image patterns to the end-user. In other embodiments, a separate dedicated storage device (not shown) may be used to store the library of known 3D objects with which to identify 3D image patterns or objects.

The Tp images are transmitted from either the acquisition system 101, or from the storage device 102, or both, to a computer system configured as a reconstruction engine 103 that reconstructs the Tp images into reconstructed image "slices" Tr, representing breast slices of selected thickness and at selected orientations, as disclosed in the above-incorporated patents and applications.

Mode filters 107 are disposed between image acquisition and image display. The filters 107 may additionally include customized filters for each type of image (i.e., Tp, Mp, and Tr images) arranged to identify and highlight certain aspects of the respective image types. In this manner, each imaging mode can be tuned or configured in an optimal way for a specific purpose. For example, filters programmed for recognizing objects across various 2D image slices may be applied in order to detect image patterns that may belong to a particular high-dimensional objects. The tuning or configuration may be automatic, based on the type of the image, or may be defined by manual input, for example through a user interface coupled to a display. In the illustrated embodiment of FIG. 1, the mode filters 107 are selected to highlight particular characteristics of the images that are best displayed in respective imaging modes, for example, geared towards identifying objects, highlighting masses or calcifications, identifying certain image patterns that may be constructed into a 3D object, or for creating 2D synthesized images (described below). Although FIG. 1 illustrates only one mode filter 107, it should be appreciated that any number of mode filters may be utilized in order to identify structures of interest in the breast tissue.

The imaging and display system 100 further includes a hierarchical multi-level feature 2D synthesizer 104 that operates substantially in parallel with the reconstruction engine 103 for generating 2D synthesized images using a combination of one or more Tp, Mp, and/or Tr images. The hierarchical multi-level feature 2D synthesizer 104 consumes a set of input images (e.g., Mp, Tr and/or Tp images), determines a set of most relevant features from each of the input images, and outputs one or more synthesized 2D images. The synthesized 2D image represents a consolidated synthesized image that condenses significant portions of various slices onto one image. This provides an end-user (e.g., medical personnel, radiologist, etc.) with the most clinically-relevant image data in an efficient manner, and reduces time spent on other images that may not have significant data.

One type of relevant image data to highlight in the synthesized 2D images would be relevant objects found across one or more Mp, Tr and/or Tp images. Rather than simply assessing image patterns of interest in each of the 2D image slices, it may be helpful to determine whether any of the 2D image patterns of interest belong to a larger high-dimensional structure, and if so, to combine the identified 2D image patterns into a higher-dimensional structure. This approach has several advantages, but in particular, by identifying high-dimensional structures across various slices/depths of the breast tissue, the end-user may be better informed as to the presence of a potentially significant structure that may not be easily visible in various 2D slices of the breast.

Further, instead of identifying similar image patterns in two 2D slices (that are perhaps adjacent to each other), and determining whether or not to highlight image data from one or both of the 2D slices, identifying both image patterns as belonging to the same high-dimensional structure may allow the system to make a more accurate assessment pertaining to the nature of the structure, and consequently provide significantly more valuable information to the end-user. Also, by identifying the high-dimensional structure, the structure can be more accurately depicted on the synthesized 2D image. Yet another advantage of identifying high-dimensional structures within the various captured 2D slices of the breast tissue relates to identifying a possible size/scope of the identified higher-dimensional structure. For example, once a structure has been identified, previously unremarkable image patterns that are somewhat proximate to the high-dimensional structure may now be identified as belonging to the same structure. This may provide the end-user with an indication that the high-dimensional structure is increasing in size/scope.

To this end, the hierarchical multi-level feature 2D synthesizer 104 creates, for a stack of image slices, a stack of object maps indicating possible locations of 3D objects. In other words, the stack of object maps depicts one or more probability regions that possibly contain high-dimensional objects. In some embodiments, the set of object maps may be used to create a high-dimensional object grid (e.g., a 3D object grid) comprising one or more high-dimensional structures (3D objects) present in the breast tissue. The stack of object maps represents a 3D volume representative of the patient's breast tissue, and identifies locations that probably hold identified 3D object(s).

However, creating object maps that identify probabilities associated with the presence of known high-dimensional objects is difficult because it may be difficult to ascertain whether a structure is an independent structure, or whether it belongs to a high-dimensional structure. Also, it may be computationally difficult and expensive to run complex algorithms to identify complicated image patterns contains in the various image slices, and identify certain image patterns as belonging to a known object. To this end, high-dimensional objects may be decomposed into lower-dimensional image patterns.

This may be achieved through a plurality of hierarchical multi-level feature modules that decompose high-dimensional objects into simpler low-level patterns. In other words, an image pattern constituting a high-level object representation can be decomposed into multiple features such as density, shape, morphology, margin, edge, line, etc. as will be described in further detail below. These decomposed representations may be computationally easier to process than the original high-level image pattern, and may help associate the lower-level image patterns as belonging to the higher-dimensional object. By decomposing more complex objects into simpler image patterns, the system enables easier detection of complex objects because it may be computationally easier to detect low-level features, while at the same time associating the low-level features to the high-dimensional object.

A high-dimensional object may refer to any object that comprises at least three or more dimensions (e.g., 3D object or higher, 3D object and time dimension, etc.). An image object may be defined as a certain type of image pattern that exists in the image data. The object may be a simple round object in a 3D space, and a corresponding flat round object in a 2D space. It can be an object with complex patterns and complex shapes, and it can be of any size or dimension. The concept of an object may extend past a locally bound geometrical object. Rather, the image object may refer to an abstract pattern or structure that can exist in any dimensional shape. It should be appreciated that this disclosure is not limited to 3D objects and/or structures, and may refer to even higher-dimensional structures. However, for simplicity, the remaining disclosure will refer to the higher-dimensional objects as 3D objects populated in a 3D grid.

The multi-level feature modules include a high-level feature module 114 to detect and identify higher-dimensional objects. For example, the high-level feature module 114 is configured to identify complex structures, such as a spiculated mass. However, it should be appreciated that the high-level feature module may require the most computational resources, and may require more complex algorithms that are programmed with a large number of filters or more computationally complex filters. Thus, in addition to directly utilizing a high-level feature module to recognize the complex structure, the 3D object may be decomposed into a range of mid-level and low-level features. Towards this end, the multi-level feature modules also include a mid-level feature module 112 configured to detect an image pattern of medium complexity, such as a center region of the spiculated mass, and a low-level feature module 110 configured to detect an even simpler image pattern, such as linear patterns radiating from the center of the spiculated mass.

Each of the multi-level feature modules (110, 112 and 114) may correspond to respective filters that comprise models, templates, and filters that enable each of the multi-level feature modules to identify respective image patterns. These multi-level feature modules are run on the input images (e.g., Tp, Tr, Mp, etc.) with their corresponding filters to identify the assigned high-level, mid-level and/or low-level features. Each hierarchical multi-level feature module (e.g., 110, 112 and 114) outputs a group of feature maps identifying areas of the respective image slice that comprise that particular feature. For example, the low-level feature module 110 may identify areas of the image slice that contains lines. The mid-level feature module 112 may identify areas of the image slice that contains circular shapes, and the high-level feature module 114 may identify areas containing the entire spiculated mass.

Figure 7A:
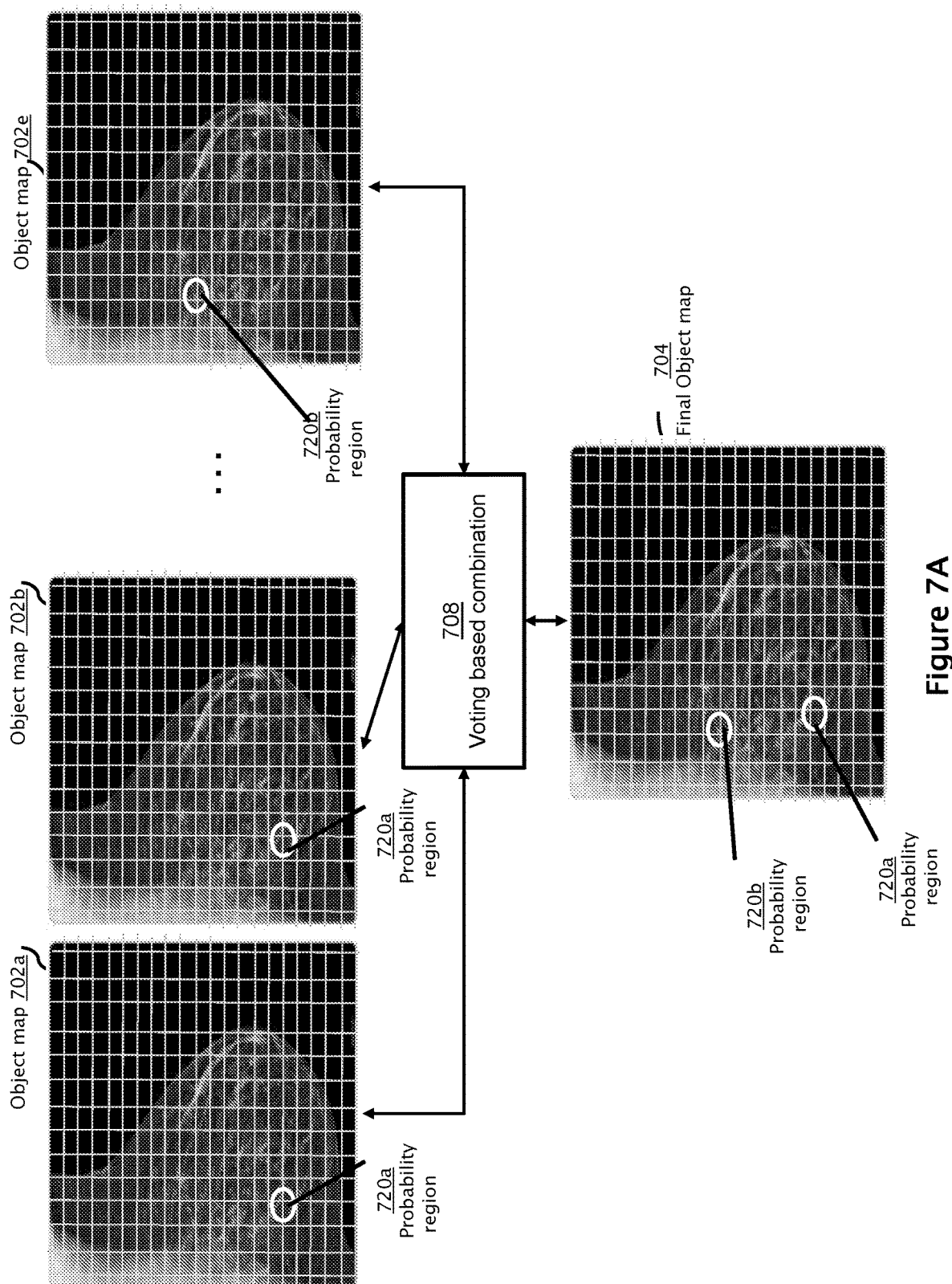

These feature maps outputted by the respective feature module may be combined using a combiner 120. The combiner 120 may be any kind of suitable combiner, e.g., a simple voting-based combiner such as shown in FIG. 7A, or a more complicated learning library-based combiner 122, such as shown in FIGS. 1 and 7B. In particular, the learning library-based combiner 120/122 generates a series of object maps 124 corresponding to each image slice, wherein the series of object maps represent the 3D volume of the patient's breast tissue and identify possible areas that contain 3D objects. In some embodiments, the stack of object maps may be utilized to create a 3D grid that identifies objects in a 3D coordinate space.

The learning library-based combiner 120/122 stores a set of known shapes/image patterns, and uses the feature maps to determine a probability of whether a particular shape exists at a 3D location. Each object map 124 is formed based on combining the various feature maps derived through the feature modules. It should be appreciated that the formed object maps 124 may identify probabilities corresponding to multiple different objects, or may simply identify probabilities corresponding to a single object. In other words, a single object map 124 corresponding to a particular image slice may identify a possible location for two different objects. Or, a single object map 124 may identify two possible locations for the same object. Thus, multiple feature maps belonging to one or more high-dimensional objects may be combined into a single object map. The hierarchical multi-level feature synthesizer 104 utilizes the stack of object maps 124, in addition to the input images (e.g., Tr, Tp, Mp, etc.) in order to create one or more synthesized 2D images, as will be discussed in further detail below.

The synthesized 2D images may be viewed at a display system 105. The reconstruction engine 103 and 2D synthesizer 104 are preferably connected to a display system 105 via a fast transmission link. The display system 105 may be part of a standard acquisition workstation (e.g., of acquisition system 101), or of a standard (multi-display) review station (not shown) that is physically remote from the acquisition system 101. In some embodiments, a display connected via a communication network may be used, for example, a display of a personal computer or of a so-called tablet, smart phone or other hand-held device. In any event, the display 105 of the system is preferably able to display respective Ms, Mp, Tr, and/or Tp images concurrently, e.g., in separate side-by-side monitors of a review workstation, although the invention may still be implemented with a single display monitor, by toggling between images.

Thus, the imaging and display system 100, which is described as for purposes of illustration and not limitation, is capable of receiving and selectively displaying tomosynthesis projection images Tp, tomosynthesis reconstruction images Tr, synthesized mammogram images Ms, and/or mammogram (including contrast mammogram) images Mp, or any one or sub combination of these image types. The system 100 employs software to convert (i.e., reconstruct) tomosynthesis images Tp into images Tr, software for synthesizing mammogram images Ms, software for decomposing 3D objects, software for creating feature maps and object maps. An object of interest or feature in a source image may be considered a 'most relevant' feature for inclusion in a 2D synthesized image based upon the application of the object maps along with one or more algorithms and/or heuristics, wherein the algorithms assign numerical values, weights or thresholds, to pixels or regions of the respective source images based upon identified/detected objects and features of interest within the respective region or between features. The objects and features of interest may include, for example, spiculated lesions, calcifications, and the like.

Figure 2:
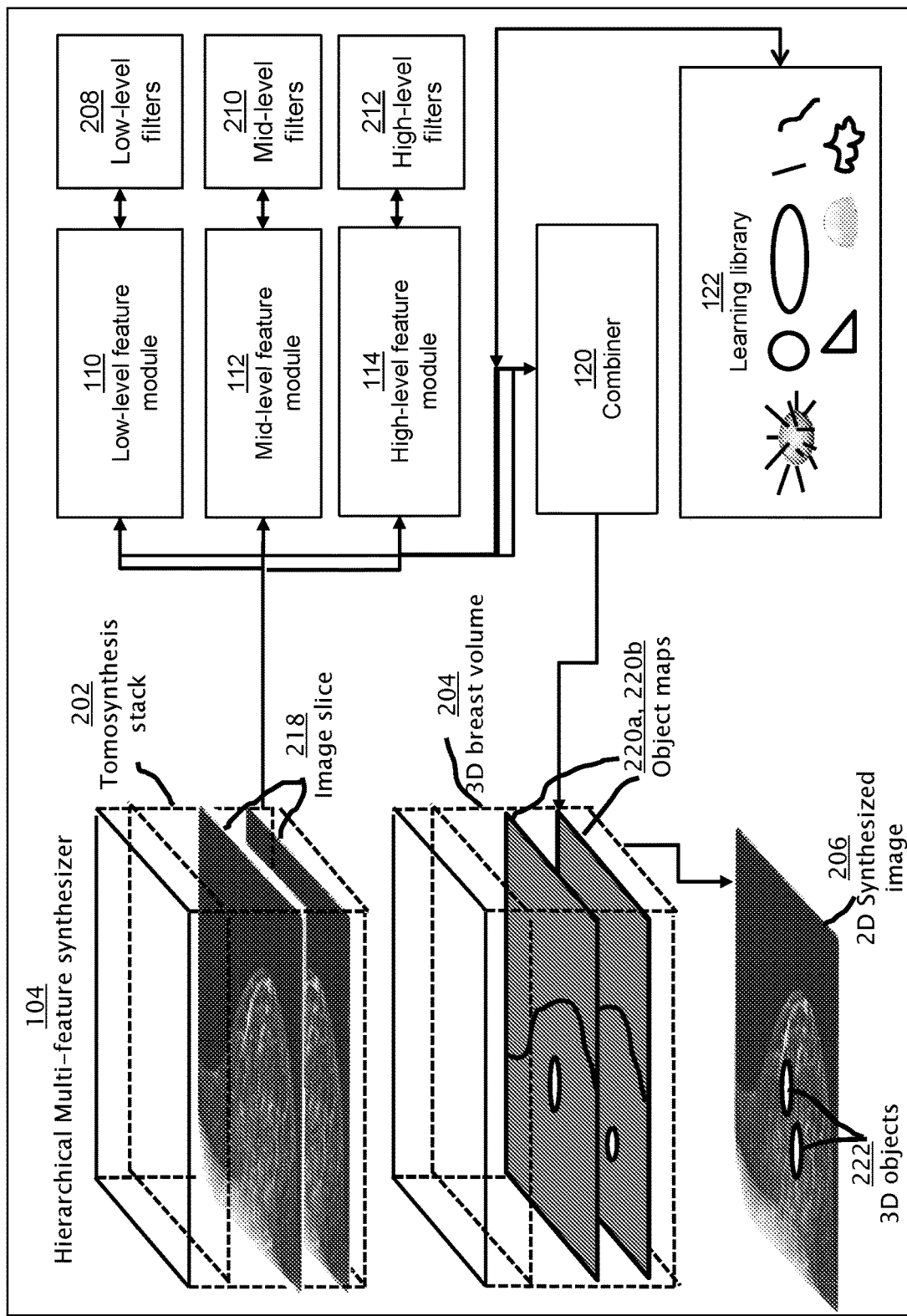
FIG. 2 is a block diagram illustrating the flow of data through a hierarchical multi-level feature synthesizer in accordance with embodiments of the disclosed inventions.

FIG. 2 illustrates the hierarchical multi-level feature synthesizer 104 in further detail. As discussed above, various image slices 218 of a tomosynthesis data set (or "stack") 202 (e.g., filtered and/or unfiltered Mp, Tr and/or Tp images of a patient's breast tissue) are directed to the hierarchical multi-level feature synthesizer 104, which are then processed to determine portions of the images to highlight in a synthesized 2D image that will be displayed on the display 105. The image slices 218 may be consecutively-captured cross-sections of a patient's breast tissue. Or, the image slices 218 may be cross-sectional images of the patient's breast tissue captured at known intervals. The tomosynthesis image stack 202 comprising the image slices 218 may be forwarded to the hierarchical multi-level feature synthesizer 104, which evaluates each of the source images in order to (1) identify high-dimensional object(s) 222 that may be identified in the image data set (Tr) for possible inclusion in one or more 2D synthesized images, and/or (2) identify respective pixel regions in the images that contain the identified object(s) 222.

As shown in the illustrated embodiment, the tomosynthesis stack 202 comprises a plurality of images 218 taken at various depths/cross-sections of the patient's breast tissue. Some of the images 218 in the tomosynthesis stack 202 comprise 2D image patterns. Thus, the tomosynthesis stack 202 comprises a large number of input images containing various image patterns within the images of the stack. For example, the tomosynthesis stack 202 may comprise one hundred images 218 captured at various depths/cross sections of the patient's breast tissue. Only a few of the images 218 may comprise any information of significance. Also, it should be noted that the tomosynthesis stack 202 simply contains 2D image patterns at various image slices 218, but it may be difficult to determine 3D structures based on the various cross-sectional images. However, the tomosynthesis stack 202 may be utilized in order to create the 3D breast volume 204 comprising the stack of object maps 124 (indicated by reference numbers 220a and 220b in FIG. 2, as explained in greater detail below).

The 3D breast volume 204 may be considered a 3D coordinate space representing a patient's breast mass. Rather than depicting 2D image patterns at various image slices, the 3D breast volume 204 depicts, through the object maps 124 (220a, 220b), probable locations of identified 3D objects in the entire mass (or portion thereof) that represents the patient's breast tissue. The object maps 214 (220a, 220b) depict, for each image slice 218, a probability that a particular object (or objects) 222 is/are present at that particular coordinate location. Rather the simply display image patterns, the stack of object maps clearly identifies particular objects in the breast volume 204. This allows for more accurate rendering of the 2D synthesized image 206 that can depict locations of objects 222 rather than simply highlight interesting image patterns (that may or may not be related to objects). Knowing that image patterns belong to particular objects 222 provides the end-user with more insight when reviewing the synthesized 2D image 206.

The object maps 124 (220a, 220b) may comprise several areas depicting a probability that an object is present at that location. For example, in the illustrated embodiment, two object maps, 220a and 220b, are shown depicting probabilities for objects at two different locations. These may refer to a single object or multiple objects, as discussed above.

The object maps 220a and 220b are created by running the image slices 218 through the various hierarchical multi-level feature modules (e.g., modules 110, 112 and 114) to produce feature maps that are then combined together in consultation with the learning library-based combiner 120/122 to determine a possible location of the respective 3D object. It should be appreciated that each 3D object may correspond to respective high-level, mid-level and low-level feature modules. Each of the multi-level feature modules outputs feature maps that identify the particular feature in the image slice. Multiple feature maps may be combined using the learning-library-based combiner 120/122 to generate an object map 220a, 220b for a particular image slice 218.

For example, in the illustrated embodiment, object maps 220a and 220b may depict probabilities for two separate objects. Although not necessarily visible in the displayed object maps 220a, 220b, themselves, when these object maps 220a and 220b are viewed as a whole for the entire tomosynthesis stack 202, the shape/size and dimensions of the various objects will become clear in the 3D breast volume 204. Thus, since two objects 222 are identified in the 3D breast volume 204, the 2D synthesized image 206 identifies their locations. It should be appreciated, however, that these two identified objects 222 may be the same object or may be multiple objects. In particular, it should be appreciated that these objects 222 may be predefined objects that the system has been trained to identify. However, even in healthy breast tissue that does not necessarily comprise any suspicious objects or structures, the 3D breast volume 204 may display a breast background object. For example, all breast linear tissue and density tissue structures can be displayed as the breast background object. For example, the 3D object grid 204 may display a "breast background" pattern throughout the 3D grid, and one or more objects may be located at various areas of the breast background. In other embodiments, "healthy" objects such as spherical shapes, oval shapes, etc., may simply be identified through the 3D object grid 204. These identified 3D objects may then be displayed on the 2D synthesized image 206; of course, out of all identified 2D objects, more clinically-significant objects may be prioritized or otherwise enhanced when displaying the respective object on the 2D synthesized image, as will be discussed in further detail below.

In one or more embodiments, the hierarchical multi-level feature synthesizer 104 utilizes both the tomosynthesis image stack 202 along with the created 3D breast volume 204 containing the stack of object maps 220 in order to condense the relevant features into a single 2D synthesized image 206. As shown in the illustrated embodiment, the 2D synthesized image 206 provides important details from multiple image slices on a single 2D synthesized image 206. Simply utilizing legacy techniques on the tomosynthesis image stack 202 may or may not necessarily provide details about both identified objects. To explain, if there is overlap in the z direction of two important image patterns, the two image patterns are essentially competing with each other for highlighting in the 2D synthesized image. If it is not determined that the two image patterns belong to two separate objects, important aspects of both objects may be compromised. Alternatively, only one of the two structures may be highlighted at all in the 2D synthesized image 206. Or, in yet another scenario, the 2D synthesized image may depict both structures as one amorphous structure such that an important structure goes entirely undetected by the end-user.

Thus, identifying objects through the stack of object maps 220a, 220b, allows the system to depict the structures more accurately in the 2D synthesized image 206, and allows for various objects to be depicted simultaneously, even if there is an overlap of various objects in the coordinate space. Thus, utilizing the 3D breast volume 204 containing the stack of object maps 220a, 220b has many advantages in producing a more accurate 2D synthesized image 206.

In one or more embodiments, the tomosynthesis image stack 202 may be used to construct the 3D breast volume 204, as discussed above. The various images of the tomosynthesis image stack 202 may be run through the multi-level feature modules (e.g., modules 110, 112 and 114). More specifically, the tomosynthesis image stack 202 may be run through a high-level module 114 that is configured to identify complex structures. For example, the high-level module 114 corresponding to 3D spiculated masses may be configured to identify the entire spiculated lesion, or complex sub-portions of spiculated lesions. The high-level module 114 may be associated with high-level filters 212 that comprise models, templates and filters that allow the high-level feature module 114 to detect the assigned feature. Although the illustrated embodiment only depicts a single high-level, mid-level and low-level feature, it should be appreciated that there may be many more multi-level feature modules per object. For example, there may be separate high-level, mid-level and low-level modules for each of the two objects depicted in the 2D synthesized image 206.

The tomosynthesis image stack 202 may also be run through the mid-level feature module 112 that may be configured to identify mid-level features. For example, the mid-level feature module 112 corresponding to 3D spiculated masses may detect circular structures representative of the centers of spiculated lesions. The mid-level feature module 112 may be associated with mid-level filters 210 that comprise models, templates and filters that allow the mid-level module 112 to detect the assigned feature.

Similarly, the tomosynthesis image stack 202 may also be run through the low-level feature module 110 that may be configured to identify much simpler low-level features. For example, the low-level feature module 110 corresponding to 3D spiculated masses may detect lines representative of linear patterns that radiate from the centers of spiculated lesions. The low-level feature module 110 may be associated with low-level filters 208 that comprise models, templates and filters that allow the low-level module 110 to detect the assigned feature.

As will be described in further detail below, each of the multi-level feature modules outputs a feature map showing areas that contain the particular feature on the image slice. These outputted feature maps for each image slice 218 may be combined using the learning library-based combiner 120/122. The learning library-based combiner 120/122 may store a plurality of known objects and may determine, based on the outputted feature maps, a probability that a particular object is located on the image slice 218. It should be appreciated that the learning library 122 will achieve greater accuracy over time, and may produce increasingly more accurate results in identifying both the location, scope and identity of respective objects 222.

The learning library-based combiner 120/122 synthesizes information gained through the various feature maps outputted by each of the hierarchical multi-level feature modules, and combines the feature maps into the object maps 220a, 220b. As discussed above, the series of object maps 220a and 220b forms the 3D breast volume 204.

Figure 3:
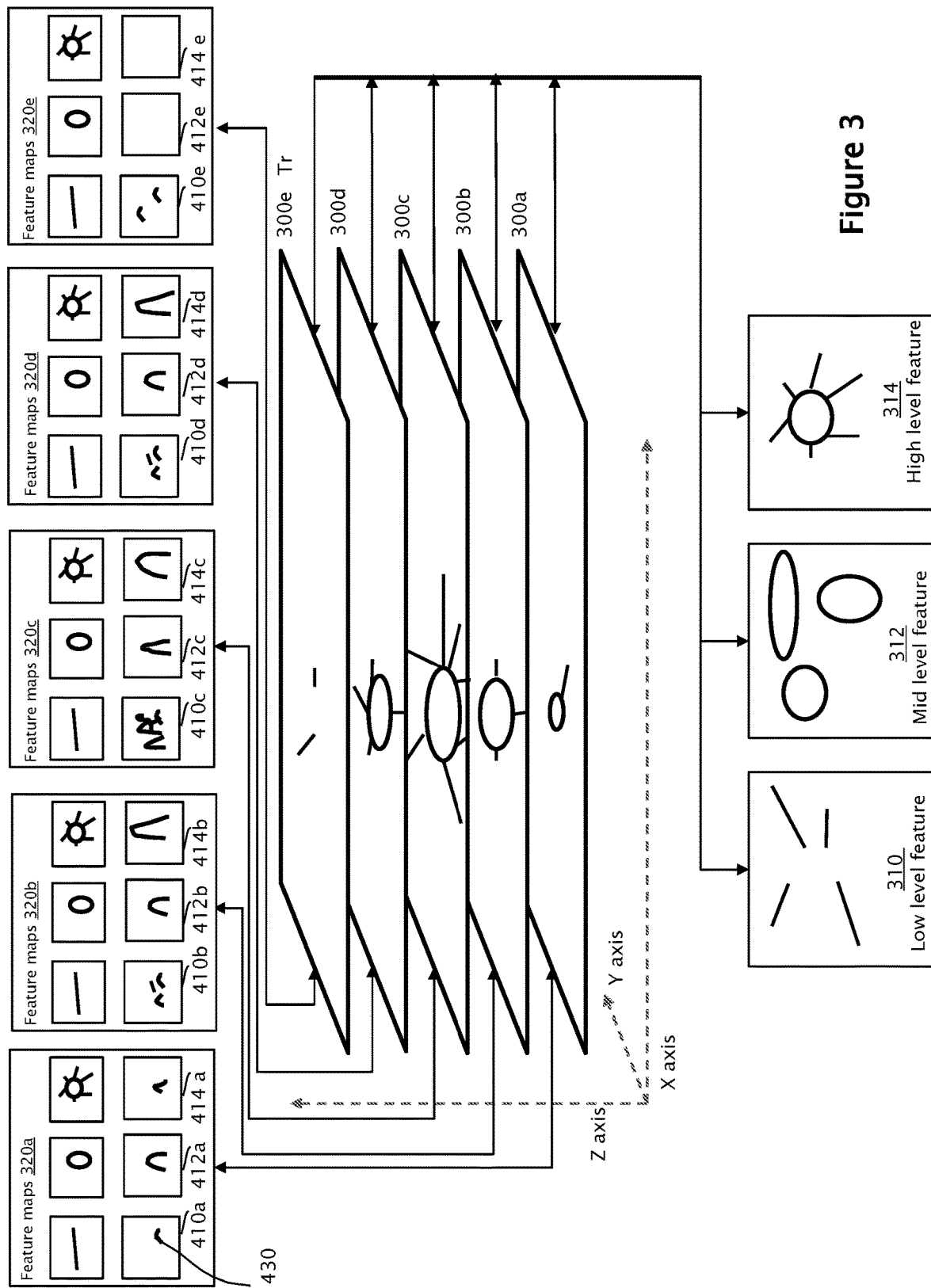
FIG. 3 illustrates one embodiment of running three multi-level feature modules associated with a high-dimensional object on a plurality of tomosynthesis images to generate a set of feature maps.

Referring now to FIG. 3, an example approach of running the various hierarchical multi-level feature modules on an example set of Tr slices is illustrated. In the illustrated embodiment, low-level feature module 310, mid-level feature module 312 and high-level feature module 314 are run on a set of Tr slices 300a-300e. Following the example from above, the low-level feature module 310 is configured to identify linear structures associated with a spiculated mass/lesion. The mid-level feature module 312 is configured to identify circular structures/arcs associated with spiculated lesions, and the high-level feature module 314 is configured to directly identify all, or almost all, spiculated lesions, i.e., structures having a spherical center as well as linear patterns emanating from the center.

When the multi-level feature modules (e.g., 310, 312 and 314) are run on the stack of Tr slices 300a-300e, a set of feature maps 320a-320e are generated. In one or more embodiments, at least three groups of feature maps (for each of the three modules) are generated for each Tr image slice. More specifically, referring to feature maps 320a, feature map 410a is generated based upon running the low-level feature module 310 (that identifies linear patterns) on Tr slice 300a. Similarly, feature map 412a is generated based upon running the mid-level feature module 312 (that identifies circular patterns) on Tr slice 300a, and feature map 414a is generated based upon running the high-level feature module 314 (that identifies the spiculated lesion) on Tr slice 300a.

Similarly, feature maps 320b (comprising 410b, 412b, and 414b) are generated by running the multi-level feature modules 310, 312 and 314 on Tr slice 300b; feature maps 320c (comprising 410c, 412c, and 414c) are generated by running the multi-level feature modules 310, 312 and 314 on Tr slice 300c; feature maps 320d (comprising 410d, 412d, and 414d) are generated by running the multi-level feature modules 310, 312 and 314 on Tr slice 300*d*; and feature maps 320*e* (comprising 410*e*, 412*e*, and 414*e*) are generated by running the multi-level feature modules 310, 312 and 314 on Tr slice 300*e*. Although not drawn to scale, each of the feature maps represents a respective coordinate system that identifies regions of the image slice containing the assigned feature.

For example, referring to feature map 410*a*, a highlighted region 430 refers to the possibility of a linear structure being present at that coordinate location of the Tr slice 300*a*. Similarly, the highlighted region of feature map 412*a* indicates areas containing a circular structure in Tr slice 300*a*, and the highlighted region of feature map 414*a* indicates an area that possibly contains an entire spiculated lesion is present in Tr slice 300*a*. As can be seen from the range of feature maps, some highlighted regions are denser than other highlighted regions. For example, feature map 414*c* shows a highlighted region indicating a strong possibility that a spiculated lesion is detected. Similarly, other feature maps (e.g., 410*b*, 410*c*, 410*d*, etc.) illustrate multiple regions indicating several detected features at various locations. If no feature is detected at a particular Tr image slice, the respective feature maps may show no highlighted regions (e.g., 412*e* and 414*e*).

Figure 4:
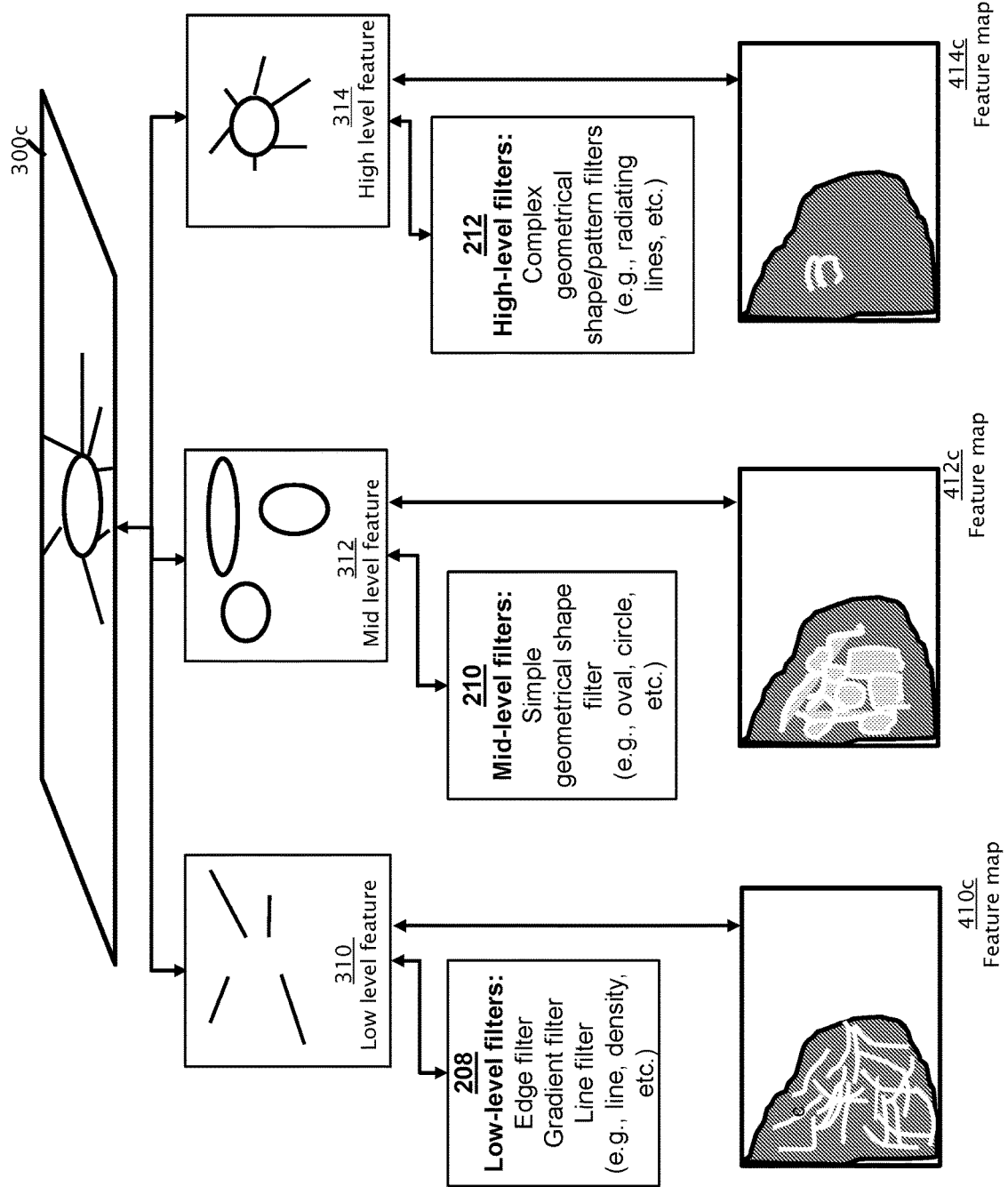
FIG. 4 illustrates one embodiment of applying filters associated with the three multi-level feature modules on one tomosynthesis image of the plurality of tomosynthesis images of FIG. 3 to generate three feature maps.

FIG. 4 illustrates an exemplary technique of running filters associated with each of the multi-level feature modules to generate respective feature maps. Specifically, FIG. 4 illustrates the low-level feature module 310, mid-level feature module 312 and high-level feature module 314, respectively, being run on Tr slice 300*c*. As discussed previously, each of the feature modules is associated with one or more filters, templates and/or models that enable the algorithms associate with the particular feature module to detect the respective shape and/or other characteristics associated with the feature module. In the illustrated embodiment, low-level feature module 310 may correspond to low-level filters 208. Although FIG. 4 describes only a few filters, it should be appreciated that any number of filters may be similarly used. Typically, the low-level filters 208 may be computationally less complex to run, and may use fewer filters and/or less complex filters when compared to the mid-level or high-level feature modules.

For example, edge filters may be used to detect edges in the image slice. Similarly, edge filters, line filters and shape filters may be used to detect linear patterns in the image slice 300*c*. Since the low-level module 310 is simply configured to detect linear patterns, these simple filters may be sufficient. When these filters are run on the image slice 300*c*, the feature map may record one or more regions that indicate a coordinate location of the line. Feature map 410*c* shows numerous regions of Tr slice 300*c* that comprise the low-level features (e.g., lines).

Similarly, the mid-level feature module 312 corresponds to the mid-level filters 210. In addition to (or instead of) the edge filters, gradient filters, line filters, and shape filters, the mid-level filter bank 210 may also comprise filters configured to recognize simple geometrical shapes. For example, the mid-level filters 210 may be configured to recognize a simple circular shape. In another embodiment, orthogonal direction filters may be configured that enable the system to determine whether an orthogonal direction of set of edges converge at a single center point. Such a combination of filters may be used to determine a region corresponding to a circular shape. The feature map 412*c* highlights regions comprising circular shapes present in image slice 300*c*.

The high-level feature module 314 corresponds to the high-level filters 212. In addition to (or instead of) filters described with respect to the low-level filters bank 208 and mid-level filters bank 210, the high-level filters 212 may comprise filters that are specifically trained to detect complex structures. These may be a combination of simple filters or more sophisticated image recognition algorithms that help detect a shape that most resembles a spiculated mass. It should be appreciated that these filters/algorithms may be computationally more complex as compared to the filters in the low-level and mid-level filters bank (e.g., 208 and 210 respectively). For example, in the illustrated embodiment, the high-level filters 208 may be configured to detect a complex geometrical shape, such as radiating lines around a circular shape. In the illustrated embodiment, the feature map 414*c* depicts regions of the image slice 300*c* containing the high-level feature. As discussed above, for each image slice, the feature maps corresponding to each of the multi-level feature modules (110, 112 and 114) are combined to form an object map depicting a probability that the particular object is present at a particular location of the image slice. The object maps are created using the learning library-based combiner 120/122, as discussed above.

Figure 5:
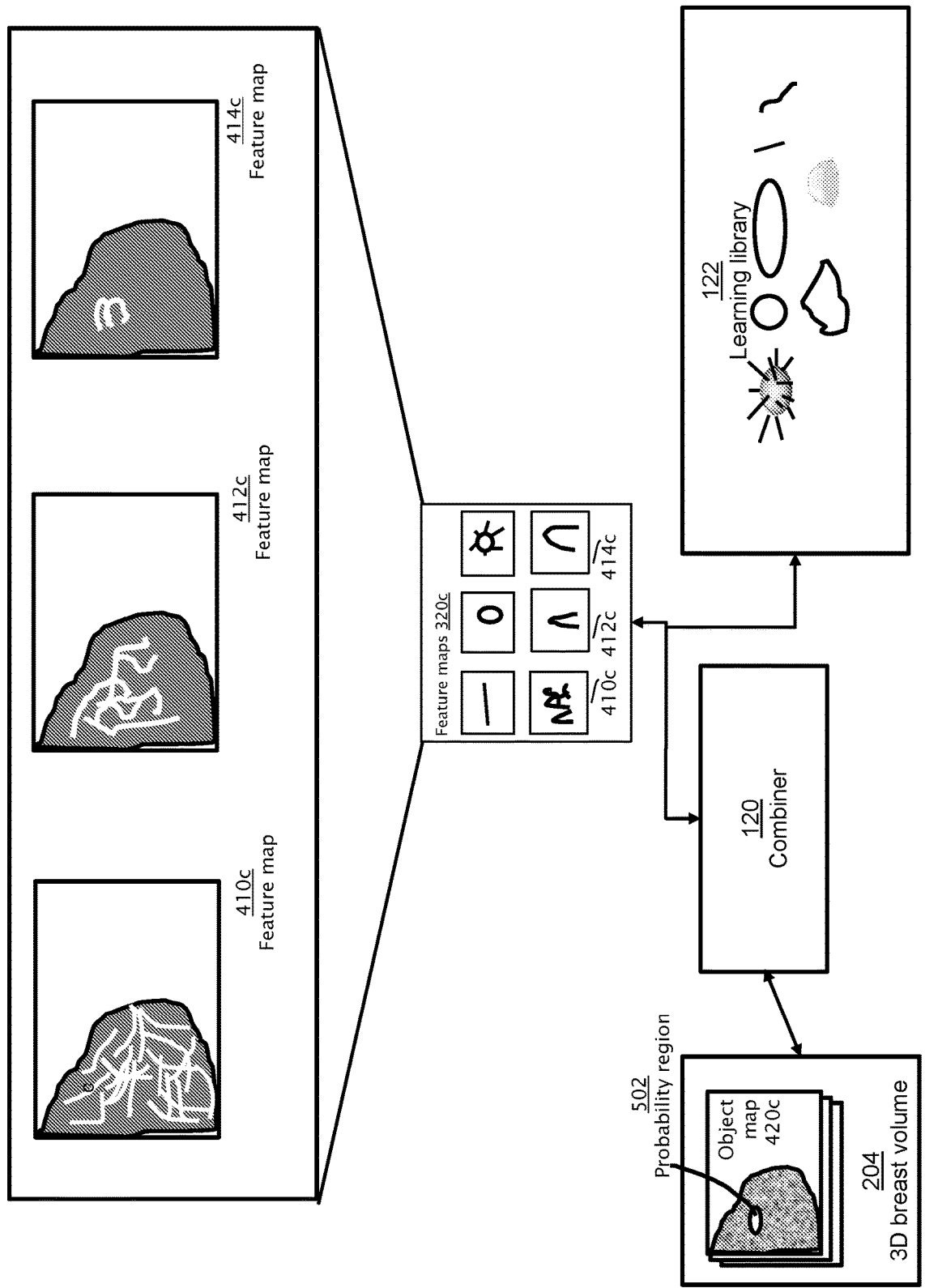
FIG. 5 illustrates one embodiment of combining feature maps into a single object map using a learning library.

FIG. 5 illustrates this combination process in further detail. In particular, FIG. 5 illustrates an exemplary approach for combining features detected through the various hierarchical multi-level feature modules is illustrated for image slice 300*c*. As shown in the illustrated embodiment, feature maps 410*c*, 412*c* and 414*c* have been created through each of the multi-level feature modules (310, 312 and 314) for image slice 300*c*. Although not shown in FIG. 5, similar feature maps may be generated for the other image slices 300*a*, 300*b*, 300*d* and 300*e* of FIG. 3. The feature maps 320*c* for image slice 300*c* are combined using the learning library-based combiner 120/122. In one or more embodiments, the learning library 122 uses machine learning techniques to improve accuracy of 3D shapes detected through the feature maps. Various machine learning algorithms may be utilized to combine information derived from the various multi-level feature modules and the feature maps to accurately generate an object map identifying a probable location of a 3D object.

The learning library-based combiner 120/122 may receive inputs from the three levels of feature maps regarding the presence of a spiculated mass. This pattern of information may help create an object map identifying a probability region 502 in the object map 420*c*. It should be appreciated that the technique described herein is simplified for illustrative purposes, and a number of complex machine learning algorithms may be used to accurately compute the probable location and dimensions of the 3D object. It should also be appreciated that machine learning algorithms employed as part of the learning library 122 may enable the system to detect and identify 3D objects using very little information as the system "learns" more over time. Thus, it is envisioned that the learning library 122 grows to be more efficient and accurate over time. For example, in one or more embodiments, weights may be assigned to feature maps derived through various feature modules in order for the system to gauge how much weight a particular feature module should be given. As the system "learns" more, the weights assigned to certain features may change.

As discussed above, the learning library-based combiner 120/122 combines information from the various feature maps in order to produce the object map 420*c* depicting the probability region 502 of a particular 3D object. For example, the probability region 502 may pertain to a location, size and scope of a spiculated mass that may be present in Tr image slice 300*c*. Similarly, the learning-library-based combiner 120/122 may output other object maps for the other image slices 300a, 300b, 300d and 300e (not shown). This stack of object maps may be used to create the 3D breast volume (such as 204 shown in FIG. 2), which helps identify one or more objects present at various 3D locations of the patient's breast tissue.

Figure 6B:
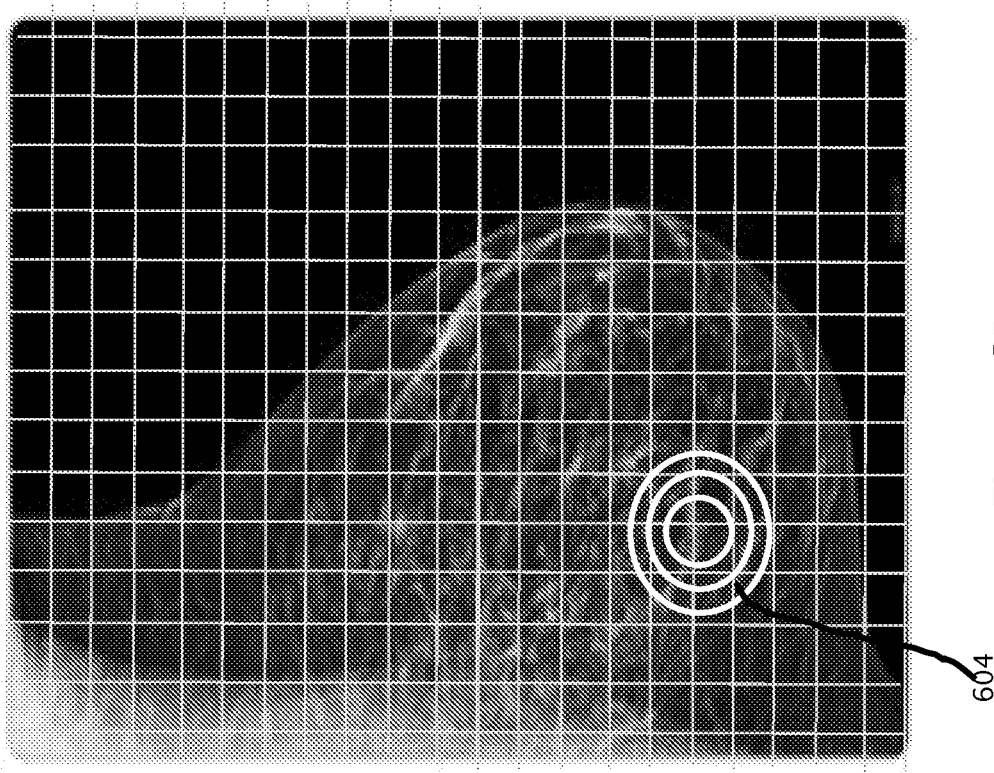
FIGS. 6A and 6B illustrate exemplary embodiments of displaying a feature on an object map.
Figure 6A:
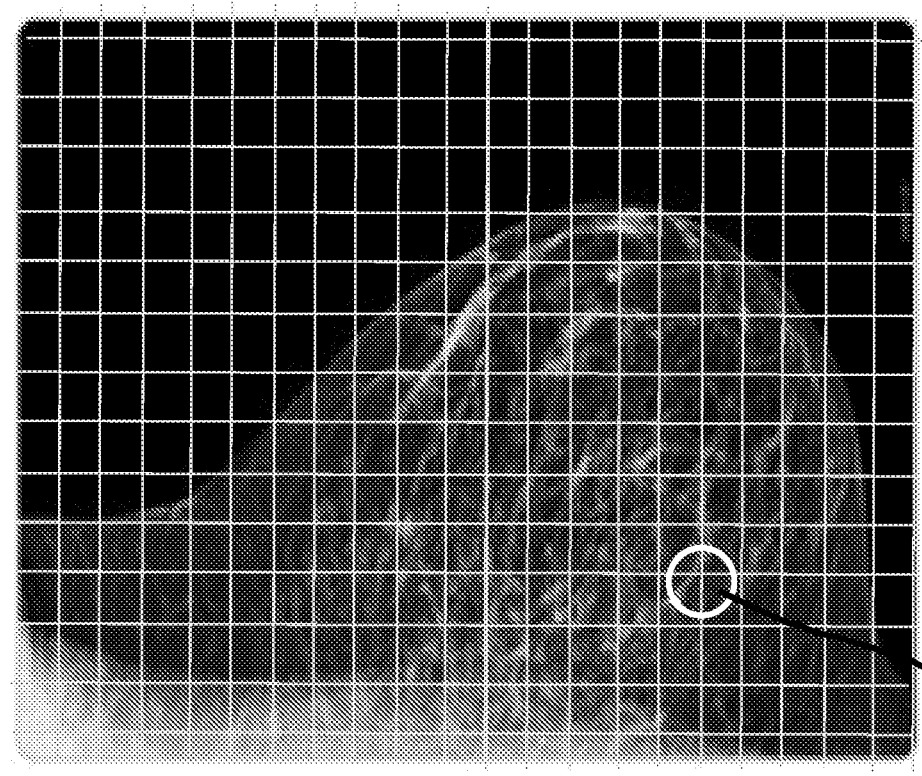

FIGS. 6A and 6B illustrate respective exemplary embodiments of depicting information on an object map. FIG. 6A simply illustrates a core of a particular object/feature of interest through a simple indicator 602, whereas FIG. 6B may provide more information through the object map by showing iso-contours of a detected object through indicator 604, which not only depicts a location of a particular object but also depicts probabilities of how large the object may be. For example, the probability that the object is at the center of indicator 604 may be the highest, and the largest circle of the indicator 704 may indicate a region of lower (but still significant) probability.

FIG. 7A illustrates an exemplary embodiment of how an alternative embodiment using a more simplified voting-based combiner 708 to determine a probability region corresponding to a 3D object in a final object map 704. In particular, the voting-based combiner 708 may be utilized on the object maps 702a-702e, so that the system "votes" on a first probability region 720a, shown in object map 702a and 702b, a second probability region 720b, shown in object map 702e, or both probability regions 720a and 720b. In the illustrated embodiment, the voting based combination may result in both probability regions 720a and 720b being highlighted in the final object map 704.

By contrast, FIG. 7B illustrates an example embodiment of the learning library-based combiner 710 to create the final object map 706. In the illustrated embodiment, even though probability object maps 702a-702e highlight different probability regions 720a and 720b (similar to the embodiment shown in FIG. 7A), a machine learning combination algorithm employed by the combiner 710 uses neural networks to select only one of the two probability regions 720a to be displayed in the final object map 706. As discussed above, when using neural networks, the system may become more sophisticated over time by "learning" patterns determined from various feature maps to construct more accurate object maps.

Figure 8:
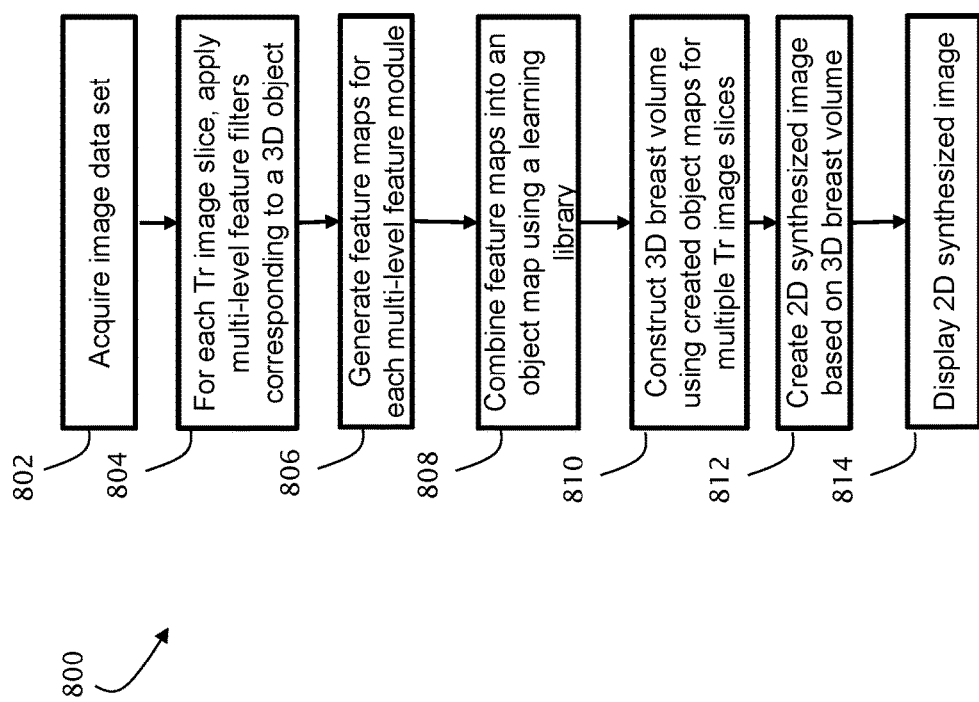
FIG. 8 illustrates an exemplary flow diagram depicting various steps to generate one or more synthesized 2D images using the high-dimensional grid.

FIG. 8 is a flow diagram 800 provided to illustrate an exemplary process that may be performed in order to create a 2D synthesized image using the plurality of object maps created through the hierarchical multi-level feature image synthesizer in accordance with one embodiment of the disclosed inventions. At step 802, an image data set is acquired. The image data set may be acquired by a tomosynthesis acquisition system, a combination tomosynthesis/mammography system, or by retrieving pre-existing image data from a storage device, whether locally or remotely located relative to an image display device. At step 804, for each 2D image slice (e.g., Tr image slice), filters associated with the various hierarchical multi-level features (e.g., a high-level feature module, a mid-level feature module and a low-level feature module) corresponding to a particular 3D object are applied.

For example, filters associated with the high-level feature module, mid-level feature module and low-level feature module may be applied to each image of the Tr stack. At step 806, feature maps are generated by each hierarchical multi-level feature module (e.g., 3 feature maps are outputted assuming there are three multi-level feature modules associated with a particular 3D object. At step 808, the feature maps generated by the high-level feature module, mid-level feature module and the low-level feature module are combined to form an object map by using a learning library. The learning library utilizes the generated feature maps to determine a probability that the particular 3D object is located at a particular location of the Tr image slice. At step 810, multiple object maps corresponding to multiple Tr image slices are stacked to create a 3D breast volume. At step 812, a synthesized 2D image is created using the plurality of object maps in the 3D breast volume. At step 814, the synthesized 2D image is displayed to the end-user.

Having described exemplary embodiments, it can be appreciated that the examples described above and depicted in the accompanying figures are only illustrative, and that other embodiments and examples also are encompassed within the scope of the appended claims. For example, while the flow diagrams provided in the accompanying figures are illustrative of exemplary steps; the overall image merge process may be achieved in a variety of manners using other data merge methods known in the art. The system block diagrams are similarly representative only, illustrating functional delineations that are not to be viewed as limiting requirements of the disclosed inventions. It will also be apparent to those skilled in the art that various changes and modifications may be made to the depicted and/or described embodiments (e.g., the dimensions of various parts), without departing from the scope of the disclosed inventions, which is to be defined only by the following claims and their equivalents. The specification and drawings are, accordingly, to be regarded in an illustrative rather than restrictive sense.

What is claimed is:

1. A method for processing breast tissue image data, comprising:
    processing image data of a patient's breast tissue to generate a set of image slices that collectively depict a patient's breast tissue;
    processing each image slice of the set of image slices to detect a first level feature of a high dimensional object present in the patient's breast tissue using an associated first-level feature module;
    generating, for each image slice, a first-level feature map depicting zero or more regions having the first-level feature;
    processing each image slice of the set of image slices to detect a second level feature of the high dimensional object present in the patient's breast tissue using an associated second-level feature module, wherein the first-level feature is a low-level feature and the second-level feature is a high-level feature;
    generating, for each image slice, a second-level feature map depicting zero or more regions having the second-level feature; and
    combining, for each image slice, the first-level feature map and the second-level feature map into an object map that indicates a probability region of the high-dimensional object in each image slice.

2. The method of claim 1, wherein the first-level feature module is configured to recognize the first-level feature by applying one or more first-level recognition models; and
    wherein the second-level feature module is configured to recognize the second-level feature by applying one or more second-level recognition models.

3. The method of claim 1, wherein the first-level feature module is configured to recognize the first-level feature by applying one or more first-level recognition templates; and wherein the second-level feature module is configured to recognize the second-level feature by applying one or more second-level recognition templates.

4. The method of claim 1, wherein the first-level feature module is configured to recognize the first-level feature by applying one or more first-level recognition filters; and
wherein the second-level feature module is configured to recognize the second-level feature by applying one or more second-level recognition filters.

5. The method of claim 1, wherein the first-level feature module is configured to recognize the first-level feature by applying one or more first-level recognition filters; and
wherein the second-level feature module is configured to recognize the second-level feature by applying one or more second-level recognition models.

6. The method of claim 1, further comprising creating a two-dimensional synthesized image of the patient's breast tissue, including identifying the high-dimensional object based at least in part on the object maps generated for each of the image slices.

7. The method of claim 1, wherein combining the first-level feature map and the second-level feature map into an object map comprises combining, by a learning library-based combiner, the first-level feature map and the second-level feature map into the object map.

8. The method of claim 7, further comprising assigning a first weight to the first-level feature map and a second weight to the second-level feature map.

9. The method of claim 8, further comprising adjusting at least one of the first weight and the second weight.

10. The method of claim 1, further comprising applying a third filter associated with a third-level feature module to each image slice of the set, the third-level feature module configured to recognize a third-level feature of a high dimensional object present in the patient's breast tissue; and
generating, for each image slice, a third-level feature map depicting zero or more regions having the third-level feature.

11. The method of claim 10, wherein the third-level feature is different from both the first-level feature and the second-level feature.

12. The method of claim 11, wherein the third-level feature is a mid-level feature.

13. The method of claim 12, wherein the probability region indicates one or more of a location, a size, and a scope of the high-dimensional object.

14. The method of claim 1, wherein the probability region comprises a probability gradient.

15. A system comprising:
a non-transitory computer-readable memory storing executable instructions; and
one or more processors in communication with the computer-readable memory, wherein, when the one or more processors execute the executable instructions, the one or more processors perform:
processing image data of a patient's breast tissue to generate a set of image slices that collectively depict a patient's breast tissue;
processing each image slice of the set of image slices to detect a first level feature of a high dimensional object present in the patient's breast tissue using an associated first-level feature module;
generating, for each image slice, a first-level feature map depicting zero or more regions having the first-level feature;
processing each image slice of the set of image slices to detect a second level feature of the high dimensional object present in the patient's breast tissue using an associated second-level feature module, wherein the first-level feature is a low-level feature and the second-level feature is a high-level feature;
generating, for each image slice, a second-level feature map depicting zero or more regions having the second-level feature; and
combining, for each image slice, the first-level feature map and the second-level feature map into an object map that indicates a probability region of the high-dimensional object in each image slice.

16. A non-transitory computer readable medium having stored theron one or more sequences of instructions for causing one or more processors to perform:
processing image data of a patient's breast tissue to generate a set of image slices that collectively depict a patient's breast tissue;
processing each image slice of the set of image slices to detect a first level feature of a high dimensional object present in the patient's breast tissue using an associated first-level feature module;
generating, for each image slice, a first-level feature map depicting zero or more regions having the first-level feature;
processing each image slice of the set of image slices to detect a second level feature of the high dimensional object present in the patient's breast tissue using an associated second-level feature module, wherein the first-level feature is a low-level feature and the second-level feature is a high-level feature;
generating, for each image slice, a second-level feature map depicting zero or more regions having the second-level feature; and
combining, for each image slice, the first-level feature map and the second-level feature map into an object map that indicates a probability region of the high-dimensional object in each image slice.

* * * * *